US010932695B2

(12) United States Patent
Pletcher et al.

(10) Patent No.: US 10,932,695 B2
(45) Date of Patent: *Mar. 2, 2021

(54) SENSING SYSTEM

(71) Applicant: Verily Life Sciences LLC, Mountain View, CA (US)

(72) Inventors: Nathan Pletcher, Mountain View, CA (US); Eric Teller, San Francisco, CA (US); Babak Amirparviz, Mountain View, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 315 days.

This patent is subject to a terminal disclaimer.

(21) Appl. No.: 15/994,025

(22) Filed: May 31, 2018

(65) Prior Publication Data

US 2018/0271408 A1    Sep. 27, 2018

Related U.S. Application Data

(63) Continuation of application No. 13/621,512, filed on Sep. 17, 2012, now Pat. No. 10,010,270.

(51) Int. Cl.
| | |
|---|---|
| *A61B 5/00* | (2006.01) |
| *A61B 5/11* | (2006.01) |
| *A61B 3/10* | (2006.01) |
| *A61B 3/113* | (2006.01) |
| *G02C 7/04* | (2006.01) |

(52) U.S. Cl.
CPC .............. *A61B 5/1103* (2013.01); *A61B 3/10* (2013.01); *A61B 3/113* (2013.01); *A61B 5/6821* (2013.01); *G02C 7/04* (2013.01); *A61B 2503/22* (2013.01)

(58) Field of Classification Search
CPC .... A61B 2017/00216; A61B 2090/373; A61B 5/1455; A61B 3/113; A61B 5/6821; A61B 3/1005; A61B 5/1103
USPC ........ 600/300, 558, 587, 595; 351/158, 210; 340/575, 576
See application file for complete search history.

(56) References Cited

U.S. PATENT DOCUMENTS

| | | | |
|---|---|---|---|
| 3,958,560 | A | 5/1976 | March |
| 4,014,321 | A | 3/1977 | March |
| 4,055,378 | A | 10/1977 | Feneberg et al. |
| 4,122,942 | A | 10/1978 | Wolfson |
| 4,136,250 | A | 1/1979 | Mueller et al. |

(Continued)

FOREIGN PATENT DOCUMENTS

| | | |
|---|---|---|
| CN | 101653354 A | 2/2010 |
| EP | 0369942 A1 | 5/1990 |

(Continued)

OTHER PUBLICATIONS

Wall, K., "Active contact lens that lets you see like the Terminator patented," Feb. 10, 2012, http://www.patexia.com/feed/active-contact-lens-that-lets-you-see-like-the-terminator-patented-2407, Last accessed Mar. 28, 2012, 5 pages.

(Continued)

*Primary Examiner* — May A Abouelela
(74) *Attorney, Agent, or Firm* — Christensen O'Connor Johnson Kindness PLLC

(57) ABSTRACT

This disclosure relates to systems and/or methods for detection of eye blinking using an active contact lens with multiple sensors and detecting orientation of the active contact lens.

17 Claims, 18 Drawing Sheets

(56) References Cited

U.S. PATENT DOCUMENTS

| | | | |
|---|---|---|---|
| 4,143,949 A | 3/1979 | Chen | |
| 4,153,641 A | 5/1979 | Deichert et al. | |
| 4,214,014 A | 7/1980 | Hofer et al. | |
| 4,309,085 A | 1/1982 | Morrison | |
| 4,312,575 A | 1/1982 | Peyman et al. | |
| 4,401,371 A | 8/1983 | Neefe | |
| 4,463,149 A | 7/1984 | Ellis | |
| 4,555,372 A | 11/1985 | Kunzler et al. | |
| 4,604,479 A | 8/1986 | Ellis | |
| 4,632,844 A | 12/1986 | Yanagihara et al. | |
| 4,686,267 A | 8/1987 | Ellis et al. | |
| 4,740,533 A | 4/1988 | Su et al. | |
| 4,826,936 A | 5/1989 | Ellis | |
| 4,973,149 A * | 11/1990 | Hutchinson | A61B 3/113 351/210 |
| 4,996,275 A | 2/1991 | Ellis et al. | |
| 4,997,770 A | 3/1991 | Giles et al. | |
| 5,032,658 A | 7/1991 | Baron et al. | |
| 5,034,461 A | 7/1991 | Lai et al. | |
| 5,070,215 A | 12/1991 | Bambury et al. | |
| 5,135,297 A | 8/1992 | Valint | |
| 5,177,165 A | 1/1993 | Valint et al. | |
| 5,177,168 A | 1/1993 | Baron et al. | |
| 5,219,965 A | 6/1993 | Valint et al. | |
| 5,260,000 A | 11/1993 | Nandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,326,584 A | 7/1994 | Kamel et al. | |
| 5,336,797 A | 8/1994 | McGee et al. | |
| 5,345,281 A * | 9/1994 | Taboada | A61B 3/113 351/209 |
| 5,346,976 A | 9/1994 | Ellis et al. | |
| 5,358,995 A | 10/1994 | Lai et al. | |
| 5,364,918 A | 11/1994 | Valint et al. | |
| 5,387,662 A | 2/1995 | Kunzler et al. | |
| 5,449,729 A | 9/1995 | Lai | |
| 5,472,436 A | 12/1995 | Fremstad | |
| 5,512,205 A | 4/1996 | Lai | |
| 5,566,067 A * | 10/1996 | Hobson | G08B 21/06 340/575 |
| 5,585,871 A | 12/1996 | Linden | |
| 5,610,252 A | 3/1997 | Bambury et al. | |
| 5,616,757 A | 4/1997 | Bambury et al. | |
| 5,638,176 A * | 6/1997 | Hobbs | G01B 11/26 356/484 |
| 5,682,210 A | 10/1997 | Weirich | |
| 5,708,094 A | 1/1998 | Lai et al. | |
| 5,710,302 A | 1/1998 | Kunzler et al. | |
| 5,714,557 A | 2/1998 | Kunzler et al. | |
| 5,726,733 A | 3/1998 | Lai et al. | |
| 5,760,100 A | 6/1998 | Nicolson et al. | |
| 5,786,765 A * | 7/1998 | Kumakura | G08B 21/06 340/576 |
| 5,908,906 A | 6/1999 | Kunzler et al. | |
| 5,981,669 A | 11/1999 | Valint et al. | |
| 6,087,941 A * | 7/2000 | Ferraz | G08B 21/06 340/575 |
| 6,131,580 A | 10/2000 | Ratner et al. | |
| 6,193,369 B1 | 2/2001 | Valint et al. | |
| 6,200,626 B1 | 3/2001 | Grobe et al. | |
| 6,213,604 B1 | 4/2001 | Valint et al. | |
| 6,312,393 B1 | 11/2001 | Abreu | |
| 6,348,507 B1 | 2/2002 | Heiler et al. | |
| 6,366,794 B1 | 4/2002 | Moussy et al. | |
| 6,423,001 B1 | 7/2002 | Abreu | |
| 6,428,839 B1 | 8/2002 | Kunzler et al. | |
| 6,431,705 B1 | 8/2002 | Linden | |
| 6,440,571 B1 | 8/2002 | Valint et al. | |
| 6,450,642 B1 | 9/2002 | Jethmalani et al. | |
| 6,532,298 B1 | 3/2003 | Cambier et al. | |
| 6,550,915 B1 | 4/2003 | Grobe | |
| 6,570,386 B2 | 5/2003 | Goldstein | |
| 6,579,235 B1 | 6/2003 | Abita et al. | |
| 6,599,559 B1 | 7/2003 | McGee et al. | |
| 6,614,408 B1 | 9/2003 | Mann | |
| 6,630,243 B2 | 10/2003 | Valint et al. | |
| 6,638,563 B2 | 10/2003 | McGee et al. | |
| 6,726,322 B2 | 4/2004 | Andino et al. | |
| 6,735,328 B1 | 5/2004 | Helbing et al. | |
| 6,749,568 B2 | 6/2004 | Fleischman et al. | |
| 6,779,888 B2 | 8/2004 | Marmo | |
| 6,804,560 B2 | 10/2004 | Nisch et al. | |
| 6,851,805 B2 * | 2/2005 | Blum | B29D 11/00826 351/159.03 |
| 6,885,818 B2 | 4/2005 | Goldstein | |
| 6,939,299 B1 | 9/2005 | Petersen et al. | |
| 6,980,842 B2 | 12/2005 | March et al. | |
| 7,018,040 B2 | 3/2006 | Blum et al. | |
| 7,131,945 B2 | 11/2006 | Fink et al. | |
| 7,169,106 B2 | 1/2007 | Fleischman et al. | |
| 7,250,197 B2 | 7/2007 | Rastogi et al. | |
| 7,384,145 B2 | 6/2008 | Hetling et al. | |
| 7,398,119 B2 | 7/2008 | Lambert et al. | |
| 7,423,801 B2 | 9/2008 | Kaufman et al. | |
| 7,429,465 B2 | 9/2008 | Muller et al. | |
| 7,441,892 B2 | 10/2008 | Hsu | |
| 7,443,016 B2 | 10/2008 | Tsai et al. | |
| 7,450,981 B2 | 11/2008 | Jeon | |
| 7,639,845 B2 | 12/2009 | Utsunomiya | |
| 7,654,671 B2 | 2/2010 | Glynn | |
| 7,699,465 B2 | 4/2010 | Dootjes et al. | |
| RE41,376 E * | 6/2010 | Torch | A61B 3/0066 340/575 |
| 7,728,949 B2 | 6/2010 | Clarke et al. | |
| 7,751,896 B2 | 7/2010 | Graf et al. | |
| 7,799,243 B2 | 9/2010 | Mather et al. | |
| 7,809,417 B2 | 10/2010 | Abreu | |
| 7,878,650 B2 | 2/2011 | Fritsch et al. | |
| 7,885,698 B2 | 2/2011 | Feldman | |
| 7,907,931 B2 | 3/2011 | Hartigan et al. | |
| 7,926,940 B2 | 4/2011 | Blum et al. | |
| 7,931,832 B2 | 4/2011 | Pugh et al. | |
| 7,964,390 B2 | 6/2011 | Rozakis et al. | |
| 8,060,560 B2 | 11/2011 | Vonog et al. | |
| 8,080,187 B2 | 12/2011 | Tepedino et al. | |
| 8,096,654 B2 | 1/2012 | Amirparviz et al. | |
| 8,118,752 B2 | 2/2012 | Hetling et al. | |
| 8,131,333 B2 | 3/2012 | Chapoy et al. | |
| 8,142,016 B2 | 3/2012 | Legerton et al. | |
| 8,169,006 B2 | 5/2012 | Kim et al. | |
| 8,215,770 B2 | 7/2012 | Blum et al. | |
| 8,224,415 B2 | 7/2012 | Budiman | |
| 8,241,574 B2 | 8/2012 | Burles et al. | |
| 8,348,422 B2 * | 1/2013 | Pugh | A61F 9/023 351/159.02 |
| 8,385,998 B2 | 2/2013 | Zhang et al. | |
| 8,446,341 B2 | 5/2013 | Amirparviz et al. | |
| 8,452,361 B2 | 5/2013 | Muller | |
| 8,461,226 B2 | 6/2013 | Meng et al. | |
| 8,480,227 B2 | 7/2013 | Qiu et al. | |
| 8,542,325 B2 | 9/2013 | Burton | |
| 8,579,434 B2 | 11/2013 | Amirparviz et al. | |
| 8,608,310 B2 | 12/2013 | Otis et al. | |
| 8,628,194 B2 | 1/2014 | Sabeta | |
| 8,636,358 B2 | 1/2014 | Binder | |
| 8,679,859 B2 | 3/2014 | Yan et al. | |
| 8,689,971 B2 | 4/2014 | Minick et al. | |
| 8,767,306 B1 | 7/2014 | Miao et al. | |
| 8,774,885 B2 | 7/2014 | Abreu | |
| 8,815,178 B2 | 8/2014 | Bishop et al. | |
| 8,823,740 B1 | 9/2014 | Amirparviz et al. | |
| 8,857,981 B2 * | 10/2014 | Pletcher | G02C 7/049 351/158 |
| 8,909,311 B2 * | 12/2014 | Ho | A61B 5/0004 600/318 |
| 8,914,089 B2 | 12/2014 | Abreu | |
| 9,114,004 B2 | 8/2015 | Fan | |
| 9,128,281 B2 | 9/2015 | Osterhout et al. | |
| 9,155,614 B2 | 10/2015 | Blum et al. | |
| 9,195,073 B2 | 11/2015 | Fritsch et al. | |
| 9,201,512 B1 * | 12/2015 | Raffle | G06F 3/033 |
| 9,296,158 B2 | 3/2016 | Pugh et al. | |

(56) References Cited

U.S. PATENT DOCUMENTS

| | | | |
|---|---|---|---|
| 9,298,020 B1* | 3/2016 | Etzkorn | G02C 7/04 |
| 9,375,885 B2 | 6/2016 | Pugh et al. | |
| 9,375,886 B2 | 6/2016 | Pugh et al. | |
| 9,474,487 B2 | 10/2016 | Chuck et al. | |
| 9,737,245 B2 | 8/2017 | Besling | |
| 2001/0028309 A1* | 10/2001 | Torch | G01S 17/88 |
| | | | 340/575 |
| 2002/0193674 A1 | 12/2002 | Fleischman et al. | |
| 2003/0021601 A1 | 1/2003 | Goldstein | |
| 2003/0069489 A1 | 4/2003 | Abreu | |
| 2003/0179094 A1 | 9/2003 | Abreu | |
| 2004/0027536 A1 | 2/2004 | Blum et al. | |
| 2004/0044418 A1 | 3/2004 | Goldstein | |
| 2004/0116794 A1 | 6/2004 | Fink et al. | |
| 2005/0045589 A1 | 3/2005 | Rastogi et al. | |
| 2005/0221276 A1 | 10/2005 | Rozakis et al. | |
| 2007/0016074 A1 | 1/2007 | Abreu | |
| 2007/0030443 A1 | 2/2007 | Chapoy et al. | |
| 2007/0121065 A1 | 5/2007 | Cox et al. | |
| 2007/0188710 A1 | 8/2007 | Hetling et al. | |
| 2008/0208335 A1 | 8/2008 | Blum et al. | |
| 2008/0218696 A1 | 9/2008 | Mir | |
| 2009/0033863 A1 | 2/2009 | Blum et al. | |
| 2009/0036761 A1 | 2/2009 | Abreu | |
| 2009/0057164 A1 | 3/2009 | Minick et al. | |
| 2009/0076367 A1 | 3/2009 | Sit et al. | |
| 2009/0118604 A1 | 5/2009 | Phan et al. | |
| 2009/0189830 A1 | 7/2009 | Deering et al. | |
| 2009/0196460 A1 | 8/2009 | Jakobs et al. | |
| 2010/0001926 A1 | 1/2010 | Amirparviz et al. | |
| 2010/0013114 A1 | 1/2010 | Bowers et al. | |
| 2010/0016704 A1 | 1/2010 | Naber et al. | |
| 2010/0028559 A1 | 2/2010 | Yan et al. | |
| 2010/0072643 A1 | 3/2010 | Pugh et al. | |
| 2010/0109175 A1 | 5/2010 | Pugh et al. | |
| 2010/0110372 A1 | 5/2010 | Pugh et al. | |
| 2010/0113901 A1 | 5/2010 | Zhang et al. | |
| 2010/0133510 A1 | 6/2010 | Kim et al. | |
| 2010/0174586 A1* | 7/2010 | Berg, Jr. | G06Q 30/02 |
| | | | 705/7.32 |
| 2010/0249548 A1 | 9/2010 | Muller | |
| 2011/0015512 A1 | 1/2011 | Pan et al. | |
| 2011/0028807 A1 | 2/2011 | Abreu | |
| 2011/0040161 A1 | 2/2011 | Abreu | |
| 2011/0055317 A1 | 3/2011 | Vonog et al. | |
| 2011/0063568 A1 | 3/2011 | Meng et al. | |
| 2011/0084834 A1 | 4/2011 | Sabeta | |
| 2011/0116035 A1 | 5/2011 | Fritsch et al. | |
| 2011/0157541 A1 | 6/2011 | Peyman | |
| 2011/0157544 A1 | 6/2011 | Pugh et al. | |
| 2011/0184271 A1 | 7/2011 | Veciana et al. | |
| 2011/0274680 A1 | 11/2011 | Mazed et al. | |
| 2011/0286064 A1 | 11/2011 | Burles et al. | |
| 2011/0298794 A1 | 12/2011 | Freedman | |
| 2012/0026458 A1 | 2/2012 | Qiu et al. | |
| 2012/0038881 A1 | 2/2012 | Amirparviz et al. | |
| 2012/0041287 A1 | 2/2012 | Goodall et al. | |
| 2012/0041552 A1 | 2/2012 | Chuck et al. | |
| 2012/0069254 A1 | 3/2012 | Burton | |
| 2012/0075168 A1 | 3/2012 | Osterhout et al. | |
| 2012/0075574 A1* | 3/2012 | Pugh | G02C 7/101 |
| | | | 351/158 |
| 2012/0078071 A1 | 3/2012 | Bohm et al. | |
| 2012/0088258 A1 | 4/2012 | Bishop et al. | |
| 2012/0092612 A1 | 4/2012 | Binder | |
| 2012/0109296 A1 | 5/2012 | Fan | |
| 2012/0140167 A1* | 6/2012 | Blum | G02C 7/04 |
| | | | 351/159.34 |
| 2012/0177576 A1 | 7/2012 | Hu | |
| 2012/0201755 A1 | 8/2012 | Rozakis et al. | |
| 2012/0245444 A1 | 9/2012 | Otis et al. | |
| 2012/0259188 A1 | 10/2012 | Besling | |
| 2012/0310339 A1* | 12/2012 | Berge | G02C 7/085 |
| | | | 623/6.22 |
| 2013/0102921 A1* | 4/2013 | Saurer | A61B 3/16 |
| | | | 600/558 |
| 2013/0258287 A1* | 10/2013 | Pugh | G02C 7/083 |
| | | | 351/210 |
| 2014/0016097 A1* | 1/2014 | Leonardi | A61B 5/6821 |
| | | | 351/209 |
| 2014/0028979 A1* | 1/2014 | De Juan, Jr. | A61F 9/00806 |
| | | | 351/247 |
| 2014/0152953 A1* | 6/2014 | Guillon | G02C 7/081 |
| | | | 351/158 |
| 2014/0192312 A1* | 7/2014 | Pletcher | A61B 3/10 |
| | | | 351/158 |
| 2014/0194708 A1* | 7/2014 | Ho | A61B 5/1495 |
| | | | 600/318 |

FOREIGN PATENT DOCUMENTS

| | | | |
|---|---|---|---|
| EP | 686372 A1 | 12/1995 | |
| EP | 1061874 A1 | 12/2000 | |
| EP | 1617757 A1 | 1/2006 | |
| EP | 1818008 A1 | 8/2007 | |
| EP | 1947501 A2 | 7/2008 | |
| EP | 2457122 A1 | 5/2012 | |
| JP | 2003-177449 A | 6/2003 | |
| JP | 2013-513127 A | 4/2013 | |
| RU | 2395228 C2 | 5/2008 | |
| WO | 1995/004609 A1 | 2/1995 | |
| WO | 2001/016641 A1 | 3/2001 | |
| WO | 2001/034312 A1 | 5/2001 | |
| WO | 2003/065876 A2 | 8/2003 | |
| WO | 2004/060431 A1 | 7/2004 | |
| WO | 2004/064629 A1 | 8/2004 | |
| WO | 2006/015315 A2 | 2/2006 | |
| WO | 2009/094643 A2 | 7/2009 | |
| WO | 2010/105728 A2 | 9/2010 | |
| WO | 2010/133317 A1 | 11/2010 | |
| WO | 2011/011344 A1 | 1/2011 | |
| WO | 2011/034592 A1 | 3/2011 | |
| WO | 2011/035228 A1 | 3/2011 | |
| WO | 2011/035262 A1 | 3/2011 | |
| WO | 2011/067391 A2 | 6/2011 | |
| WO | 2011/083105 A1 | 7/2011 | |
| WO | 2011/163080 A1 | 12/2011 | |
| WO | 2012/035429 A2 | 3/2012 | |
| WO | 2012/037455 A1 | 3/2012 | |
| WO | 2012/051167 A1 | 4/2012 | |
| WO | 2012/051223 A2 | 4/2012 | |
| WO | 2012/052765 A2 | 4/2012 | |
| WO | 2012/061411 A1 | 5/2012 | |

OTHER PUBLICATIONS

Parviz, Babak A., "Augmented Reality in a Contact Lens," IEEE Spectrum, Sep. 2009, http://spectrum.ieee.org/biomedical/bionics/augmented-reality-in-a-contact-lens/0, Last accessed Mar. 14, 2012, 6 pages.

Bionic contact lens 'to project emails before eyes,' http://www.kurzweilai.net/forums/topic/bionic-contact-lens-to-project-emails-before-eyes, Last accessed Mar. 14, 2012, 2 pages.

Tweedie, et al., "Contact creep compliance of viscoelastic materials via nanoindentation," J. Mater. Res., Jun. 2006, vol. 21, No. 2, pp. 1576-1589, Materials Research Society.

Brahim, et al., "Polypyrrole-hydrogel composites for the construction of clinically important biosensors," 2002, Biosensors & Bioelectronics, vol. 17, pp. 53-59.

Huang, et al., "Wrinkling of Ultrathin Polymer Films," Mater. Res. Soc. Symp. Proc., 2006, vol. 924, 6 pages, Materials Research Society.

Zarbin, et al., "Nanotechnology in ophthalmology," Can J Ophthalmol, 2010, vol. 45, No. 5, pp. 457-476.

Selner, et al., "Novel Contact Lens Electrode Array for Multi-electrode Electroretinography (meERG)," IEEE, 2011, 2 pages.

Liao, et al., "A 3-μW CMOS Glucose Sensor for Wireless Contact-Lens Tear Glucose Monitoring," IEEE Journal of Solid-State Circuits, Jan. 2012, vol. 47, No. 1, pp. 335-344.

(56) References Cited

OTHER PUBLICATIONS

Chen, et al., "Microfabricated Implantable Parylene-Based Wireless Passive Intraocular Pressure Sensors," Journal of Microelectromechanical Systems, Dec. 2008, vol. 17, No. 6, pp. 1342-1351.
Thomas, et al., "Functional Contact Lenses for Remote Health Monitoring in Developing Countries," IEEE Global Humanitarian Technology Conference, 2011, pp. 212-217, IEEE Computer Society.
Pandey, et al., "A Fully Integrated RF-Powered Contact Lens With a Single Element Display," IEEE Transactions On Biomedical Circuits And Systems, Dec. 2010, vol. 4, No. 6, 8 pages.
Lingley, et al., "Multipurpose integrated active contact lenses," SPIE, 2009, 2 pages.
Chu, et al., "Soft Contact-lens Sensor for Monitoring Tear Sugar as Novel Wearable Device of Body Sensor Network," http://www.ksi.edu/seke/dms11/DMS/2_Kohji_Mitsubayashi.pdf, Last accessed Jul. 27, 2012, 4 pages.
Liao, et al., "A 3μW Wirelessly Powered CMOS Glucose Sensor for an Active Contact Lens," 2011 IEEE International Solid-State Circuits Conference, Session 2, Feb. 21, 2011, 3 pages.
Hurst, "How contact lenses could help save your life," Mail Online, Apr. 19, 2010, http://www.dailymail.co.uk/health/article-1267345/How-contact-lenses-help-save-life.html, Last accessed Jul. 27, 2012.
Lončar, et al., "Design and Fabrication of Silicon Photonic Crystal Optical Waveguides," Journal of Lightwave Technology, Oct. 2000, vol. 18, No. 10, pp. 1402-1411.
Liu, et al., "Miniature Amperometric Self-Powered Continuous Glucose Sensor with Linear Response," Analytical Chemistry, 7 pages.
Baxter, "Capacitive Sensors," 2000, 17 pages.
Lingley, et al., "A Single-Pixel Wireless Contact Lens Display," Journal of Micromechanics and Microengineering, 2011, 9 pages.
"Polyvinylidene fluoride," Wikipedia, http://en.wikipedia.org/wiki/Polyvinylidene_fluoride, Last accessed Mar. 30, 2012, 4 pages.
Murdan, "Electro-responsive drug delivery from hydrogels," Journal of Controlled Release, 2003, vol. 92, pp. 1-17.
Haders, "New Controlled Release Technologies Broaden Opportunities for Ophthalmic Therapies," Drug Delivery Technology, Jul./Aug. 2009, vol. 8, No. 7, pp. 48-53.
Singh, et al., "Novel Approaches in Formulation and Drug Delivery using Contact Lenses," Journal of Basic and Clinical Pharmacy, May 2011, vol. 2, Issue 2, pp. 87-101.
"Contact Lenses: Look Into My Eyes," The Economist, Jun. 2, 2011, http://www.economist.com/node/18750624/print, Last accessed Mar. 13, 2012, 8 pages.
Holloway, "Microsoft developing electronic contact lens to monitor blood sugar," Gizmag, Jan. 5, 2012, http://www.gizmag.com/microsoft-electronic-diabetic-contact-lens/20987/, Last accessed Mar. 13, 2012, 5 pages.
Adler, "What types of statistical analysis do scientists use most often?" O'Reilly Community, Jan. 15, 2010, 2 pages, http://broadcast.oreilly.com/2010/01/what-types-of-statistical-anal.html, Last accessed Sep. 4, 2012.
Bull, "Different Types of Statistical Analysis," Article Click, Feb. 4, 2008, 4 pages, http://www.articleclick.com/Article/Different-Types-Of-Statistical-Analysis/968252, Last accessed Sep. 4, 2012.
"Understanding pH measurement," Sensorland, 8 pages, http://www.sensorland.com/HowPage037.html, Last accessed Sep. 6, 2012.
"Regression analysis," Wikipedia, 11 pages, http://en.wikipedia.org/wiki/Regression_analysis, Last accessed Sep. 6, 2012.
"Statistics," Wikipedia, 10 pages, http://en.wikipedia.org/wiki/Statistics, Last accessed Sep. 6, 2012.
"Nonlinear regression," Wikipedia, 4 pages, http://en.wikipedia.org/wiki/Nonlinear_regression, Last accessed Sep. 10, 2012.
"Linear regression," Wikipedia, 15 pages, http://en.wikipedia.org/wiki/Linear_regression, Last accessed Sep. 10, 2012.
"Integrated circuit," Wikipedia, 9 pages, http://en.wikipedia.org/wiki/Integrated_circuit, Last accessed Sep. 10, 2012.
"Photolithography," Wikipedia, 8 pages, http://en.wikipedia.org/wiki/Photolithography, Last accessed Sep. 10, 2012.
"Alcohol Detection Technologies: Present and Future," American Beverage Institute, 9 pages.
Harding, et al., "Alcohol Toxicology for Prosecutors: Targeting Hardcore Impaired Drivers," American Prosecutors Research Institute, Jul. 2003, 40 pages.
Kim, et al., "Oral Alcohol Administration Disturbs Tear Film and Ocular Surface," American Academy of Ophthalmology, 2012, 7 pages.
CN 201380048403.7—Second Office Action with English Translation, dated Nov. 2, 2016, 25 pages.
RU 2015114333—Notice of Allowance with English Translation, dated Oct. 18, 2016, 18 pages.
JP 2015-532120—Office Action with English Translation, dated Nov. 4, 2016, 7 pages.
Badugu, et al., "A Glucose Sensing Contact Lens: A Non-Invasive Technique for Continuous Physiological Glucose Monitoring," Journal of Fluorescence, Sep. 2003, pp. 371-374, vol. 13, No. 5.
Carlson, et al., "A 20 mV Input Boost Converter With Efficient Digital Control for Thermoelectric Energy Harvesting," IEEE Journal of Solid-State Circuits, Apr. 2010, pp. 741-750, vol. 45, No. 4.
Chu, et al., "Biomedical soft contact-lens sensor for in situ ocular biomonitoring of tear contents," Biomed Microdevices, 2011, pp. 603-611, vol. 13.
Chu, et al., "Soft contact lens biosensor for in situ monitoring of tear glucose as non-invasive blood sugar assessment," Talanta, 2011, pp. 960-965, vol. 83.
Ho, et al., "Contact Lens With Integrated Inorganic Semiconductor Devices," MEMS 2008. IEEE 21st International Conference on IEEE, 2008, pp. 403-406.
Lähdesmäki, et al., "Possibilites for Continuous Glucose Monitoring by a Functional Contact Lens," IEEE Instrumentation & Measurement Magazine, Jun. 2010, pp. 14-17.
Lingley, et al., "A contact lens with integrated micro solar cells," Microsyst Technol, 2012, pp. 453-458, vol. 18.
Parviz, Babak A., "For Your Eyes Only," IEEE Spectrum, Sep. 2009, pp. 36-41.
Saeedi, et al., "Self-assembled crystalline semiconductor optoelectronics on glass and plastic," J. Micromech. Microeng., 2008, pp. 1-7, vol. 18.
Extended European Search Report dated Jan. 7, 2019 for European Application No. 18196913.0, filed Sep. 16, 2013, 6 pages.
Indian Office Action, dated Dec. 16, 2019, in corresponding Indian Patent Application No. 2169/CHENP/2015, 5 pages.
Saeedi, et al., "Self-Assembled Inorganic Micro-Display on Plastic," Micro Electro Mechanical Systems, 2007. MEMS. IEEE 20th International Conference on IEEE, 2007, pp. 755-758.
Sensimed Triggerfish, Sensimed Brochure, 2010, 10 pages.
Shih, Yi-Chun, et al., "An Inductorless DC-DC Converter for Energy Harvesting With a 1.2-μW Bandgap-Referenced Output Controller," IEEE Transactions on Circuits and Systems—II: Express Briefs, Dec. 2011, pp. 832-836, vol. 58, No. 12.
Shum, et al., "Functional modular contact lens," Proc. of SPIE, 2009, pp. 73970K-1 to 73970K-8, vol. 7397.
Stauth, et al., "Self-assembled single-crystal silicon circuits on plastic," PNAS, Sep. 19, 2006, pp. 13922-13927, vol. 103, No. 38.
Yao, et al., "A contact lens with integrated telecommunication circuit and sensors for wireless and continuous tear glucose monitoring," J. Micromech. Microeng., 2012, pp. 1-10, vol. 22.
Yao, et al., "A Dual Microscal Glucose Sensor on a Contact Lens, Tested in Conditions Mimicking the Eye," Micro Electro Mechanical Systems (MEMS), 2011 IEEE 24th International Conference on IEEE, 2011, pp. 25-28.
Yao, et al., "A contact lens with embedded sensor for monitoring tear glucose level," Biosensors and Bioelectronics, 2011, pp. 3290-3296, vol. 26.
Yao, et al., "A Soft Hydrogel Contact Lens with an Encapsulated Sensor for Tear Glucose Monitoring," Micro Electro Mechanical Systems (MEMS), 2012 IEEE 25th International Conference on IEEE, 2012, pp. 769-772.
Yeager, et al., "A 9 μA, Addressable Gen2 Sensor Tag for Biosignal Acquisition," IEEE Journal of Solid-State Circuits, Oct. 2010, pp. 2198-2209, vol. 45, No. 10.

(56) References Cited

OTHER PUBLICATIONS

Zhang, et al., "Design for Ultra-Low Power Biopotential Amplifiers for Biosignal Acquisition Applications," IEEE Transactions on Biomedical Circuits and Systems, 2012, pp. 344-355, vol. 6, No. 4.
JP 2015-532120—Office Action with English Translation, dated Mar. 18, 2016, 6 pages.
CN 201380048403.7—Office Action with English Translation, dated Mar. 2, 2016, 17 pages.
AU 2013315114—Notice of Acceptance, mailed Feb. 19, 2016, 2 pages.
EP 13837832.8—Extended European Search Report, dated May 30, 2016, 8 pages.
RU 2015114333—First Office Action with Search Report, dated May 31, 2016, 7 pages.
International Searching Authority, International Preliminary Report on Patentability for PCT/US2013/059923 dated Mar. 26, 2015, 11 pages.
AU 2013315114—Examination Report, dated Oct. 19, 2015, 3 pages.
International Searching Authority, International Search Report and Written Opinion for PCT/US2013/059923 dated Jan. 24, 2014, 15 pages.
Brazilian Patent Application No. BR112015005824-8, with English Translation, mailed Jul. 9, 2020, 6 pages.

* cited by examiner

US 10,932,695 B2

SENSING SYSTEM

REFERENCE TO RELATED APPLICATION

This application is a continuation of U.S. application Ser. No. 13/621,512, filed on Sep. 17, 2012, the contents of which are incorporated herein by reference.

TECHNICAL FIELD

This disclosure generally relates to systems and methods for employing multiple sensors on a contact lens for detecting blinks and contact lens orientation.

DETAILED DESCRIPTION

Overview

Figure 1A:
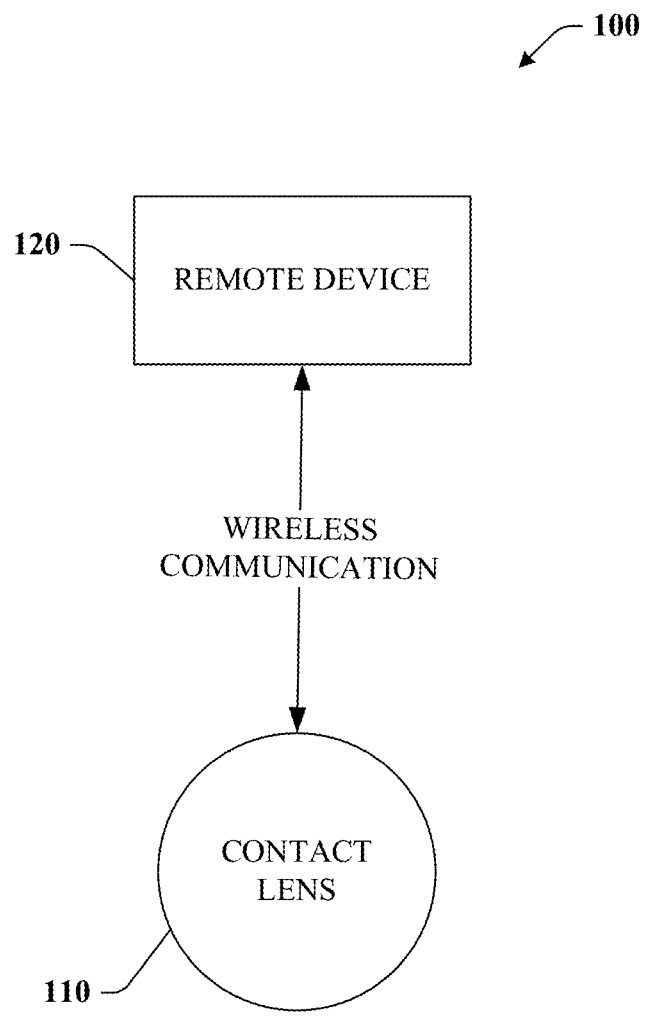
FIG. 1A illustrates a diagram of an exemplary non-limiting system for system for detecting eye blinking or contact lens orientation using a multi-sensor contact lens in accordance with an implementation of this disclosure.

Various aspects or features of this disclosure are described with reference to the drawings, wherein like reference numerals are used to refer to like elements throughout. In this specification, numerous specific details are set forth in order to provide a thorough understanding of this disclosure. It should be understood, however, that certain aspects of this disclosure may be practiced without these specific details, or with other methods, components, materials, etc. In other instances, well-known structures and devices are shown in block diagram form to facilitate describing this disclosure.

In accordance with various disclosed aspects, a mechanism is provided for detecting blinking of an eye via multiple sensors on or within the contact lens (hereinafter referred to as multi-sensor contact lens). For example, a multi-sensor contact lens can be placed in one or both eyes of a user that can actively determine (or infer) blinking of the eye. In a non-limiting example, multi-sensor contact lens monitors sensors on or within the multi-sensor contact lens at intervals that are less than an average or shortest length of time of an eye blink. It is to be appreciated that both eyes of a human user generally blink at the same time, and thus in various embodiments only one multi-sensor contact lens is needed. In another embodiment, two such multi-sensor contact lenses can be employed such that a user can selectively blink one or both eyes, for example to generate a command to a remote device. In yet another embodiment, the multi-sensor contact lens can be employed in connection with non-human users (e.g., dogs or other species with eyes). Furthermore, detected (or inferred) blinking can include determination or inference of full or partial eye blinks. It is to be appreciated that components on or within a contact lens can be of a shape, size, opacity, and/or positioned so as not to obstruct vision through an opening of a pupil of an eye when worn.

In accordance with other disclosed aspects, a mechanism is provided for detecting orientation of a multi-sensor contact lens. For example, a multi-sensor contact lens can be placed in one or both eyes of a user that can actively determine (or infer) their respective orientations. In a non-limiting example, multi-sensor contact lens monitors sensors on or within the multi-sensor contact lens and based upon an order which they enter a state indicative of being covered or uncovered by an eyelid, determines (or infers) orientation of the multi-sensor contact lens.

Referring now to the drawings, FIG. 1A depicts a system 100 for detecting (or inferring) eye blinking or contact lens orientation using a multi-sensor contact lens. System 100 includes a multi-sensor contact lens 110 that determines (or infers) blinking of an eye on which the multi-sensor contacts lens is worn or orientation of the multi-sensor contact lens. In addition, multi-sensor contact lens 110 can utilize information regarding the determined (or inferred) blinking of the eye (hereinafter referred to as "eye blink information") or orientation of the multi-sensor contact lens (hereinafter referred to as "orientation information") locally to control features of multi-sensor contact lens 110 (e.g., issuing commands, adjusting content presentation, activating or deactivating options or components, or any other suitable function). Furthermore, multi-sensor contact lens 110 can optionally communicate eye blink information and/or orientation information to a remote device 120 for employment in connection with operations associated with the remote device 120 (e.g., adjusting content presentation, controlling a user interface, activating or deactivating options or components, requesting instructions or information, issuing commands, or any other suitable function). Multi-sensor contact lens 110 and remote device 120 can also receive input from users, for example to control interaction with and presentation of content, see e.g., FIG. 8 and corresponding disclosure.

Figure 8:
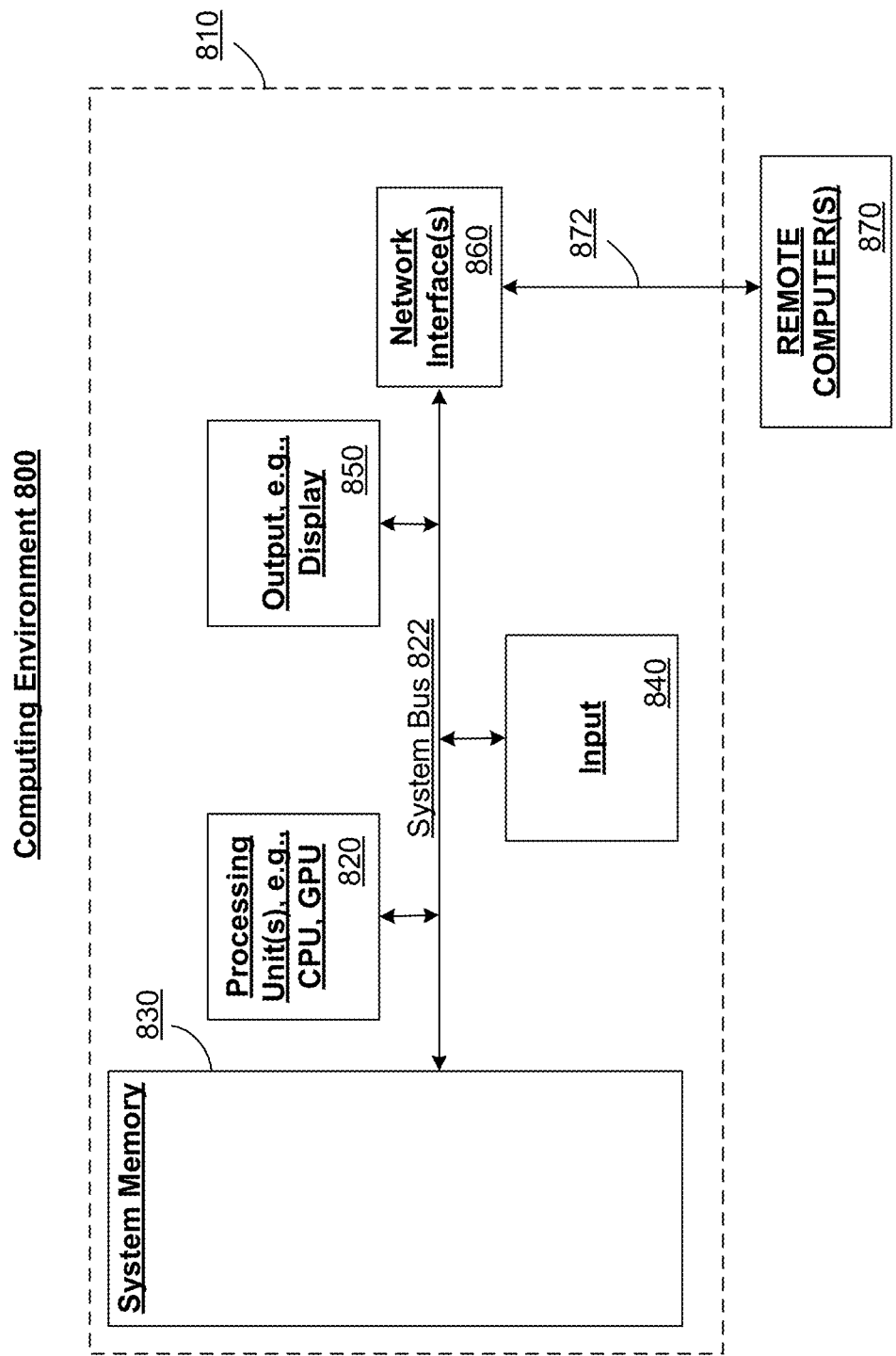
FIG. 8 is a block diagram representing an exemplary non-limiting computing system or operating environment in which the various embodiments can be implemented.

Multi-sensor contact lens 110 and remote device 120, respectively include a memory that stores computer executable components and a processor that executes computer executable components stored in the memory (see e.g., FIG. 8). Multi-sensor contact lens 110 and remote device 120 can communicate via a wireless network. It is to be appreciated that while only one remote device 120 is depicted, multi-sensor contact lens 110 can communicate with any suitable number of remote devices 120 concurrently, serially, an ad hoc manner, or in accordance with any suitable protocol. Additionally, remote device 120 can communicate with any suitable number of multi-sensor contact lenses 110 concurrently, serially, an ad hoc manner, or in accordance with any suitable protocol.

Remote device 120, can include a wearable device or a non-wearable device. Wearable device can include, for example, heads-up display glasses, a monocle, eyeglasses, sunglasses, a headset, a visor, a cap, a helmet, a mask, a headband, clothing, or any other suitable device that can be worn by a human or non-human user and can communicate with multi-sensor contact lens 110 remotely. Non-wearable device can include, for example, a mobile device, a mobile phone, a camera, a camcorder, a video camera, personal data assistant, laptop computer, tablet computer, desktop computer, server system, cable set top box, satellite set top box, cable modem, television set, monitor, media extender device, blu-ray device, DVD (digital versatile disc or digital video disc) device, compact disc device, video game system, portable video game console, audio/video receiver, radio device, portable music player, navigation system, car stereo, or any suitable device that can communicate with multi-sensor contact lens 110 remotely. Moreover, remote device 120 and multi-sensor contact lens 110 can include a display and/or user interface (e.g., a web browser or application), that can generate, receive and/or present graphical indicia (e.g., displays, text, video . . . ) generated locally or remotely.

Figure 1B:
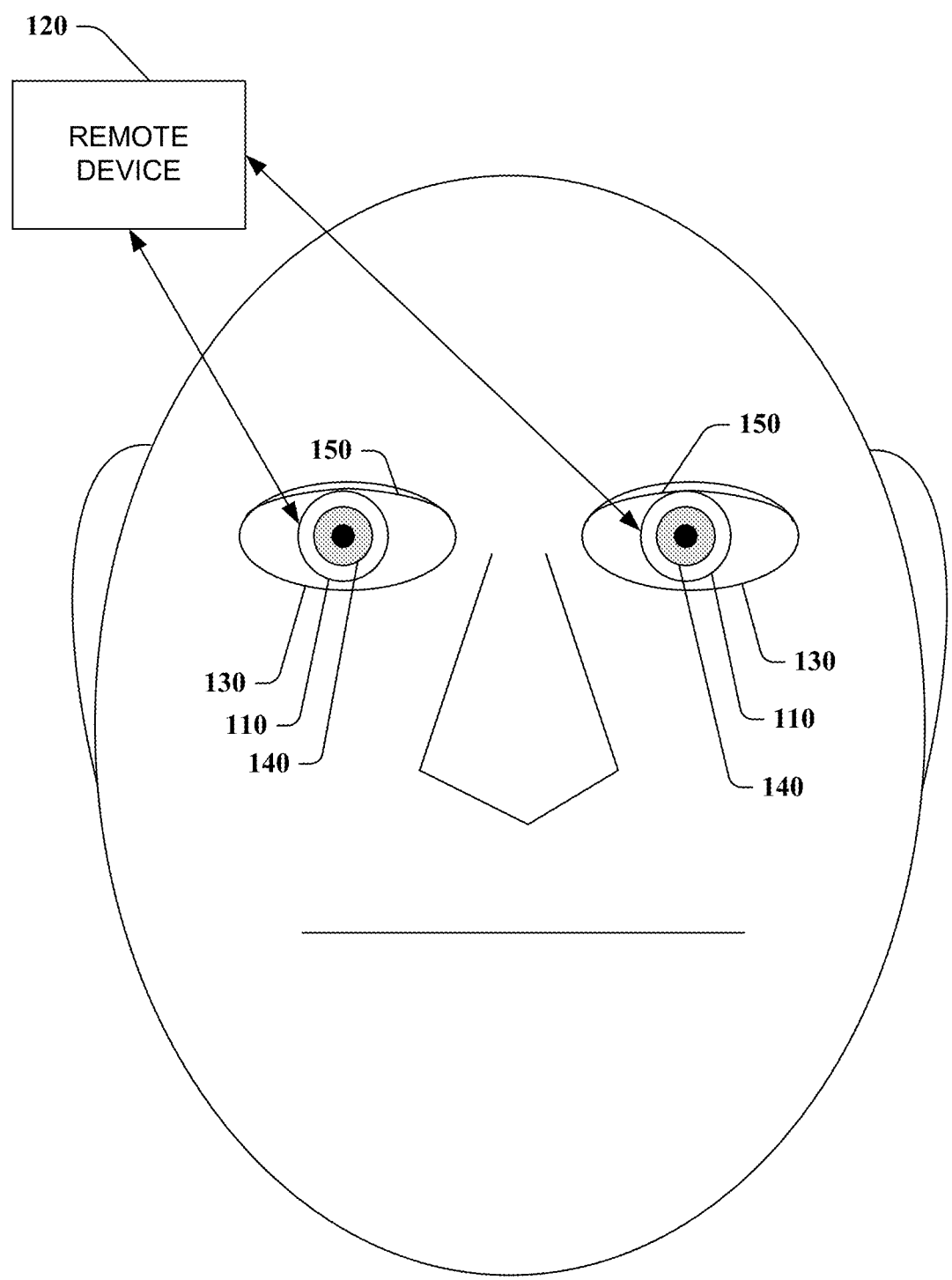
FIG. 1B illustrates a diagram of the exemplary non-limiting system of FIG. 1A worn on both eyes of a human user in accordance with an implementation of this disclosure.

Referring to FIG. 1B, system 100 is depicted on a human user. Multi-sensor contact lenses 110 are shown worn on both eyes 130, covering irises 140 while eyelids 150 are open. Remote device 120 is shown with one or more transceivers (not shown) arranged to communicate wirelessly with multi-sensor contact lenses 110. It is to be further appreciated that respective transceivers of remote device 120 can have transmission power and/or signal reception sensitivity suitable for transmitting a signal to and receiving a signal from an associated multi-sensor contact lenses 110 on an eye without interfering with another multi-sensor contact lenses 110 on another eye. While FIG. 1B depicts a multi-sensor contact lenses 110 arrangement in both eyes, it is to be appreciated that an arrangement with a multi-sensor contact lens 110 on one eye can be employed.

Figure 2A:
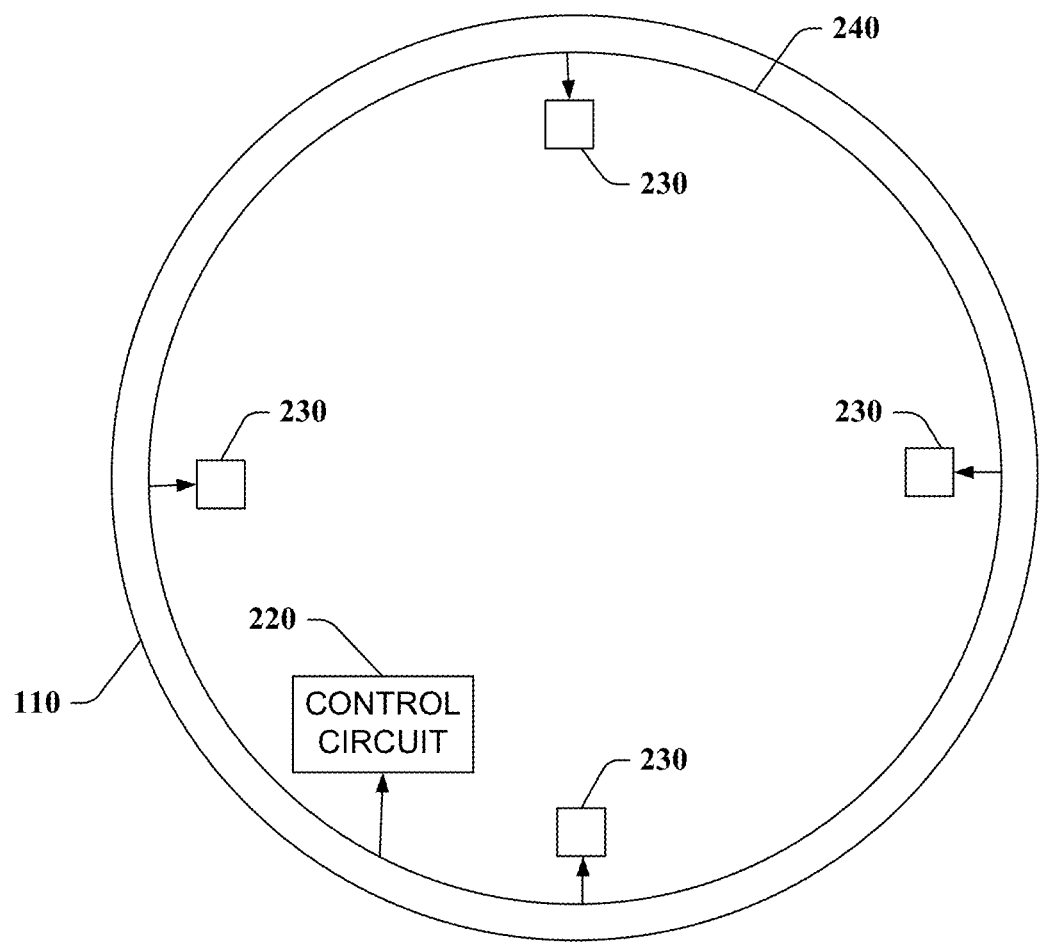
FIG. 2A illustrates a diagram of an exemplary non-limiting multi-sensor contact lens accordance with an implementation of this disclosure.

Referring to FIG. 2A, multi-sensor contact lens 110 is depicted that includes, disposed on or within its substrate, a control circuit 220 and two or more sensors 230 (in this example, four sensors 230 equally spaced around the periphery of multi-sensor contact lens 110). Control circuit 220 and sensors 230 are coupled wirelessly or via wire by coupling 240. It should be noted that all or some sensors 230 can have independent coupling to control circuit 220. It is to be further appreciated that different aspects of interaction between control circuit 220 and sensors 230 may be respectively coupled via wire or wirelessly. In one example, all interactions are coupled via wire. In another example, all interactions are coupled wirelessly. In a further example, some interactions are coupled wirelessly, while other interactions are coupled via wire. For example, communication interaction may be coupled wirelessly, while power supply interactions may be coupled via wire. Sensor 230 can be any suitable sensor that changes state based on a condition that changes according to sensor 230 being covered or uncovered by eyelid 150 during blinking of eye 130. For example, sensor 230 can be a photodiode that changes state based upon an amount of light received at the photodiode, such as difference in amount of light incident on the photodiode when an eyelid 150 covers the photodiode versus not covering the photodiode. In another example, sensor 230 can be a pressure sensor that changes state according to pressure change caused by an eyelid 150 covering or uncovering sensor 230. In a further example, sensor 230 can be a conductivity sensor that changes state according to changes in conductivity from a tear film caused by an eyelid 150 covering or uncovering sensor 230. In an additional example, sensor 230 can be a temperature sensor that changes state according to a change in temperature as a tear film caused by an eyelid 150 covering or uncovering sensor 230 evaporates. In a further example, sensor 230 can be an electric field sensor that changes state according changes in static charge or capacitance caused by an eyelid 150 covering or uncovering sensor 230. It is to be appreciated that sensors 230 can respectively be uniquely identifiable to control circuit 220, for example, via an identifier signal or identifying information conveyed from respective sensors 230 to control circuit 220.

Figure 2B:
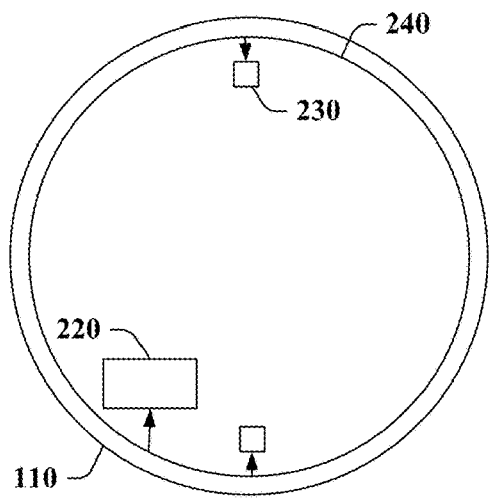
FIG. 2B illustrates a diagram of an exemplary non-limiting multi-sensor contact lens with two sensors respectively aligned at top and bottom of multi-sensor contact lens in accordance with an implementation of this disclosure.
Figure 2C:
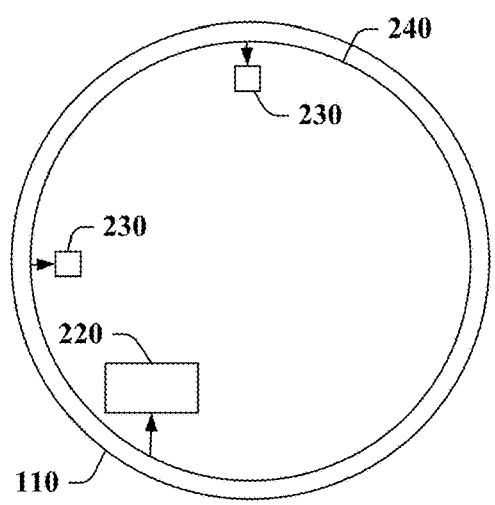
FIG. 2C illustrates a diagram of an exemplary non-limiting multi-sensor contact lens with two sensors respectively aligned at a bottom and one side of multi-sensor contact lens in accordance with an implementation of this disclosure.
Figure 2D:
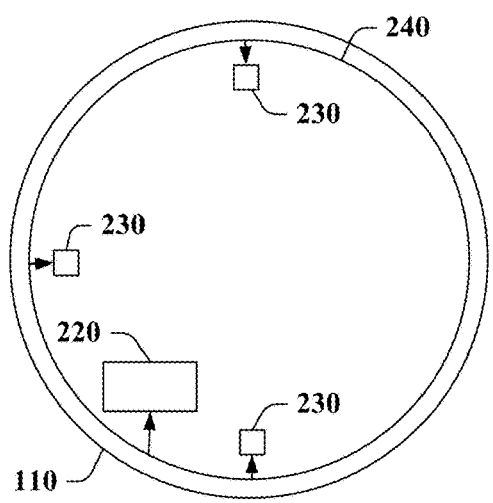
FIG. 2D illustrates a diagram of an exemplary non-limiting multi-sensor contact lens with three sensors respectively aligned at top, bottom, and one side of multi-sensor contact lens in accordance with an implementation of this disclosure.
Figure 2E:
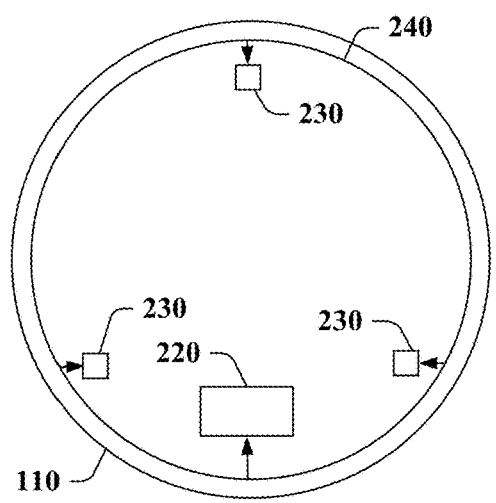
FIG. 2E illustrates a diagram of an exemplary non-limiting multi-sensor contact lens with three sensors aligned in an equilateral triangular shape near the periphery of multi-sensor contact lens in accordance with an implementation of this disclosure.
Figure 2F:
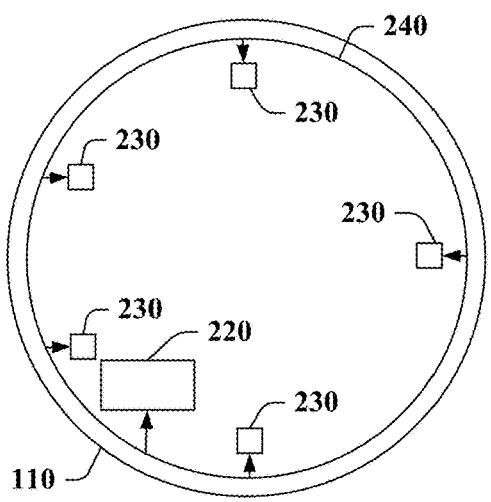
FIG. 2F illustrates a diagram of an exemplary non-limiting multi-sensor contact lens with five sensors aligned in a pentagon shape near the periphery of multi-sensor contact lens in accordance with an implementation of this disclosure.
Figure 2G:
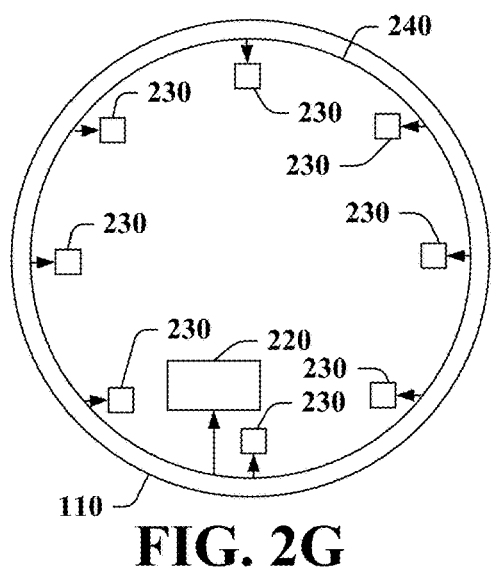
FIG. 2G illustrates a diagram of an exemplary non-limiting multi-sensor contact lens with eight sensors aligned in a regular octagon shape near the periphery of multi-sensor contact lens in accordance with an implementation of this disclosure.

Referring to FIGS. 2B-G, various exemplary configurations of sensors 230 on or within a multi-sensor contact lens 110 are depicted. In an embodiment, multi-sensor contact lens 110 can be weighted to self-align into a particular position when worn, similar to toric contact lenses. For example, sensors 230 may require specific positioning in order to detect eye blinks. In another embodiment, multi-sensor contact lens 110 are not weighted. For example, sufficient sensors 230 can be employed in an arrangement, such as four sensors 230 equally spaced around a periphery of multi-sensor contact lens 110 to detect a blink in most any orientation of the multi-sensor contact lens 110. In another example, a determined (or inferred) orientation of the multi-sensor contact lens 110 as discussed below can be employed in detecting a blink. FIG. 2B shows a multi-sensor contact lens 110 with two sensors 230 respectively aligned at top and bottom of multi-sensor contact lens 110. FIG. 2C depicts a multi-sensor contact lens 110 with two sensors respectively aligned at a bottom and one side of multi-sensor contact lens 110. FIG. 2D depicts a multi-sensor contact lens 110 with three sensors 230 respectively aligned at top, bottom, and one side of multi-sensor contact lens 110. FIG. 2E illustrates a multi-sensor contact lens 110 with three sensors 230 aligned in an equilateral triangular shape near the periphery of multi-sensor contact lens 110. FIG. 2F depicts a multi-sensor contact lens 110 with five sensors 230 aligned in a pentagon shape near the periphery of multi-sensor contact lens 110. FIG. 2G illustrates a multi-sensor contact lens 110 with eight sensors 230 aligned in a regular octagon shape near the periphery of multi-sensor contact lens 110. Employing a plurality of uniquely identifiable sensors 230 allows for detecting partial eye blinks or an amount of eye blink, and orientation of the multi-sensor contact lens 110 as discussed below. It is to be appreciated that any suitable number of sensors 230 can be respectively placed in any suitable locations of multi-sensor contact lens 110. It is to be appreciated that increasing number of sensors 230, for example distributed around the periphery of the multi-sensor contact lens 110 or linearly across one or more portions of the multi-sensor contact lens 110, can increase precision or granularity of determining (or inferring) an amount of eye blink or orientation of the multi-sensor contact lens 110.

Figure 2H:
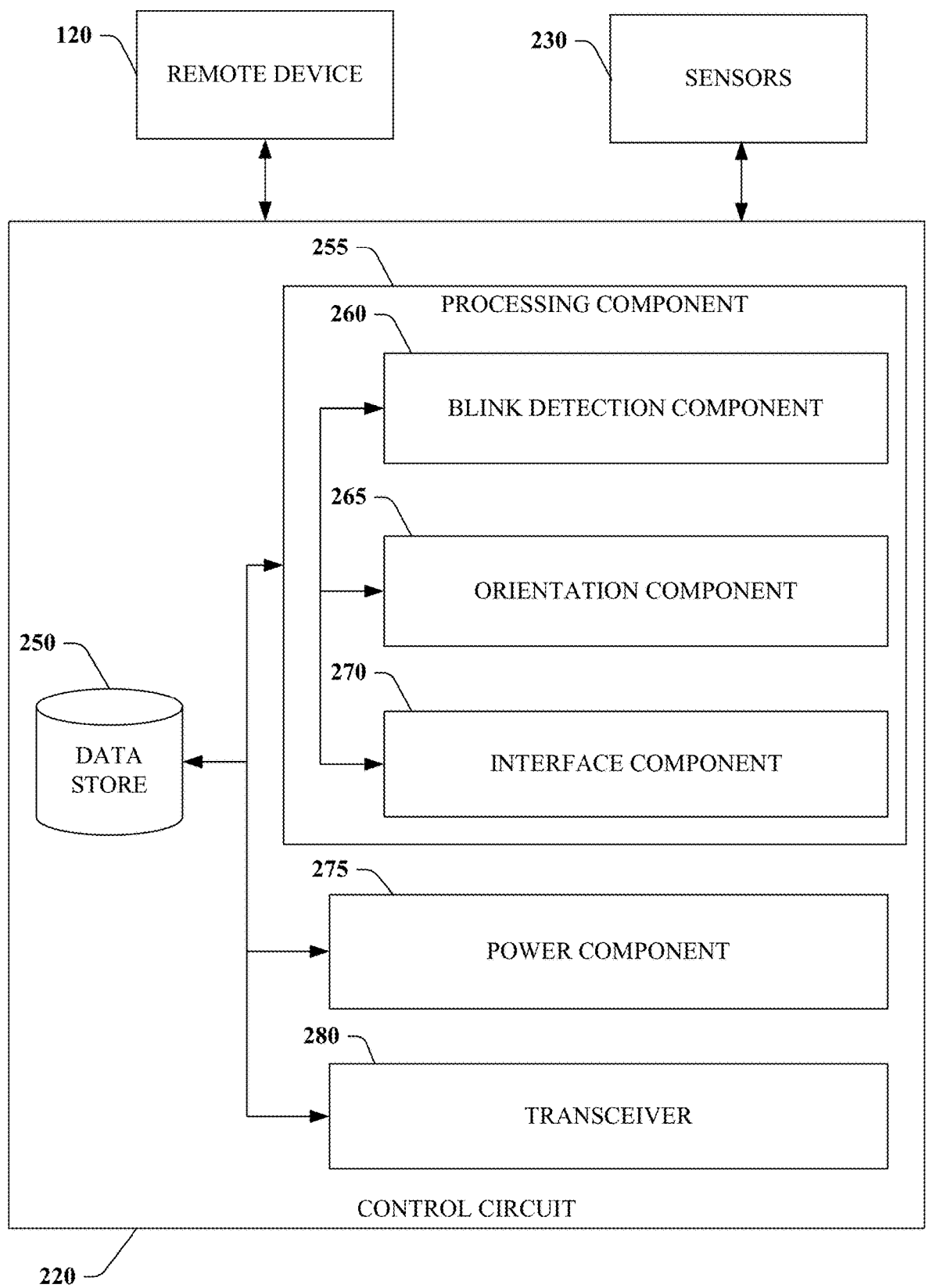
FIG. 2H illustrates a diagram of an exemplary non-limiting control circuit in accordance with an implementation of this disclosure.

Referring to FIG. 2H, is depicted control circuit 220 that includes processing component 255 that determines (or infers) blinking of an eye, orientation of multi-sensor contact lens 110, and communicates with remote device 120 and sensors 230. In addition, control circuit 220 can include power component 275 that manages, receives, generates, stores, and/or distributes electrical power to other components of multi-sensor contact lens 110. Control circuit 220 can also include one or more transceivers 280 for transmitting or receiving signals to or from remote device 120 or sensors 230. It is to be appreciated that sensors 230 can interface directly with processing component 255 without need to employ transceiver 280, for example through a wired coupling.

Additionally, control circuit 220 can include a data store 250 that can store data from processing component 255, power component 275, transceiver 280, remote device 120, or sensors 230. Data store 250 can reside on any suitable type of storage device, non-limiting examples of which are illustrated with reference to FIGS. 7 and 8, and corresponding disclosure.

With continued reference to FIG. 2H, processing component 255 includes blink detection component 260 that determines (or infers) blinking of an eye based upon state information from sensors 230 indicative of being covered or uncovered by eyelid 150. It is to be appreciated that blink detection component 260 can pull state information from sensors 230 or can automatically have state information pushed by sensors 230. It is further to be appreciated that blink detection component 260 can determine (or infer) state information based upon signals or information received from sensors 230. In an embodiment, blink detection component 260 can continuously monitor sensors 230. In another embodiment, blink detection component 260 can periodically monitor sensors 230. In a non-limiting example, blink detection component 260 can monitor sensors 230 at intervals that are less than an average or shortest length of time of an eye blink to avoid missing detection of a blink. For example, if the average human user has a blink that is N milliseconds, blink detection component 260 can monitor sensors 230 at an interval less than N milliseconds. In another example, if the shortest blink for a human user is M milliseconds, blink detection component 260 can monitor sensors 230 at an interval less than M milliseconds. It is to be appreciated that any suitable interval for monitoring sensors 230 can be employed.

Figure 3A:
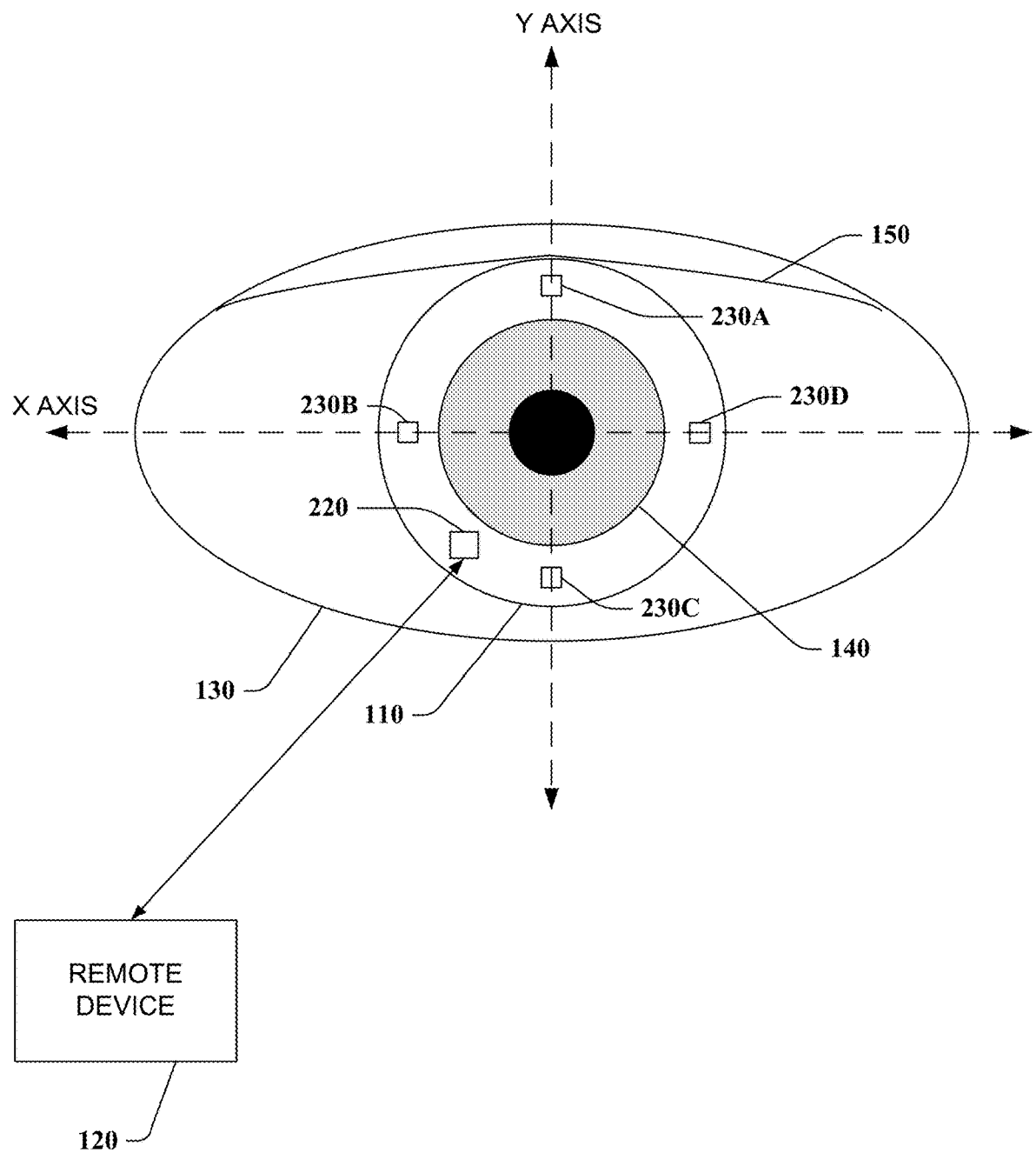
FIG. 3A illustrates a diagram of a close-up view of a portion of the exemplary non-limiting system of FIG. 1B being worn by a human user with eyelid open using four sensors in accordance with an implementation of this disclosure.

Referring to FIG. 3A, is depicted a close-up of FIG. 1B of a portion of eye 130 wearing a multi-sensor contact lens 110 with four sensors in a configuration as illustrated in FIG. 2A equally spaced around the periphery of multi-sensor contact lens 110. It is to be appreciated that respective sensors 230A-D are uniquely identifiable to blink detection component 260. In this example, the four sensors 230 are oriented with sensors 230B and 230D aligned on a horizontal axis X and sensors 230A and 230C aligned on a vertical axis Y. Axis X and Y have an origin at the geometric center of multi-sensor contact lens 110. In this example, eyelid 150 is open. As such, blink detection component 260 obtains state information corresponding to sensors 230A-D not being covered by eyelid 150.

Figure 3B:
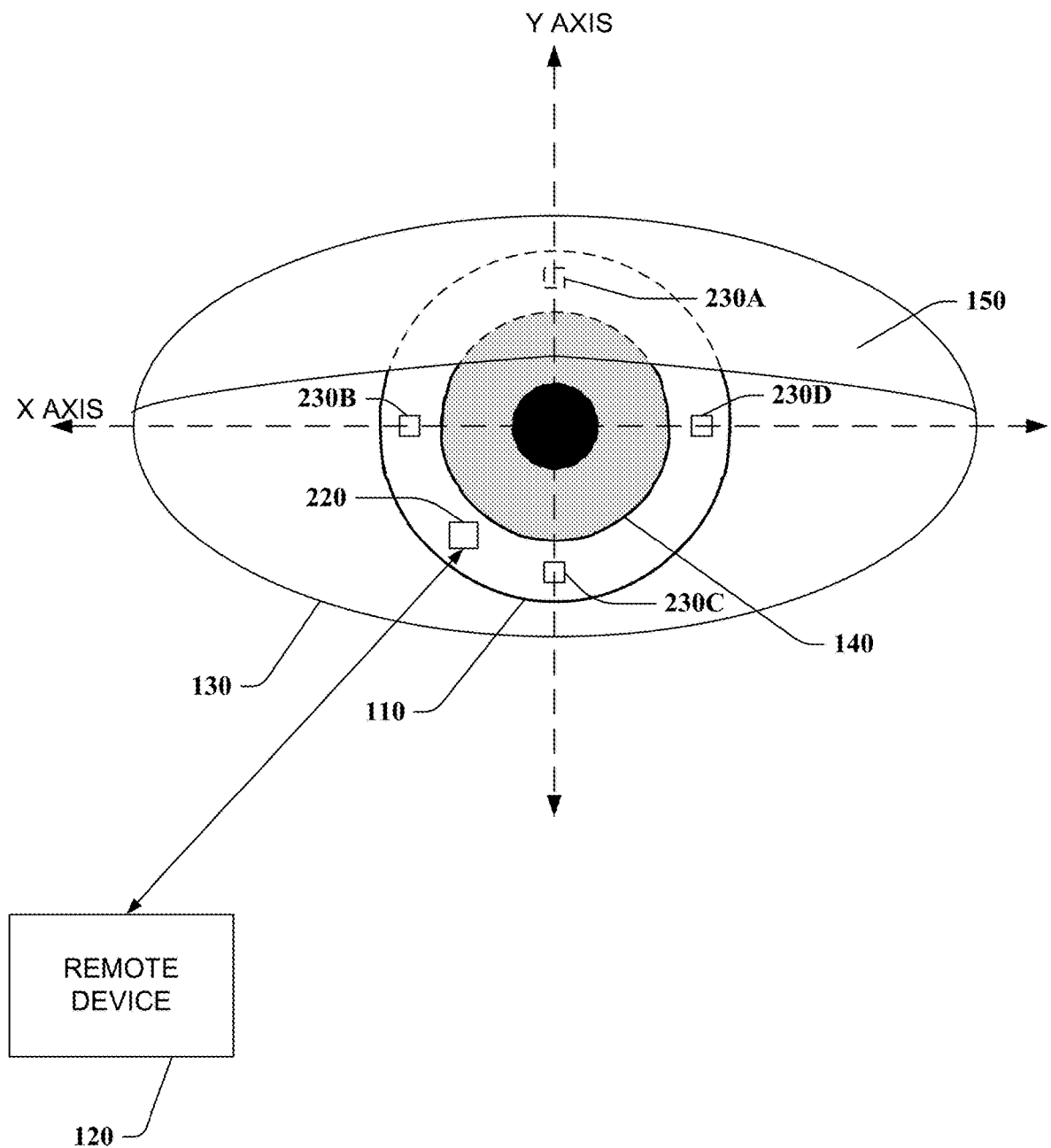
FIG. 3B illustrates a diagram of the close-up view of the portion of the exemplary non-limiting system of FIG. 3A with the eyelid partially closed in accordance with an implementation of this disclosure.

FIG. 3B corresponds to FIG. 3A with eyelid 150 partially closed. As such, blink detection component 260 obtains state information corresponding to sensor 230A covered by eyelid 150 and sensors 230B-D not covered by eyelid 150.

Figure 3C:
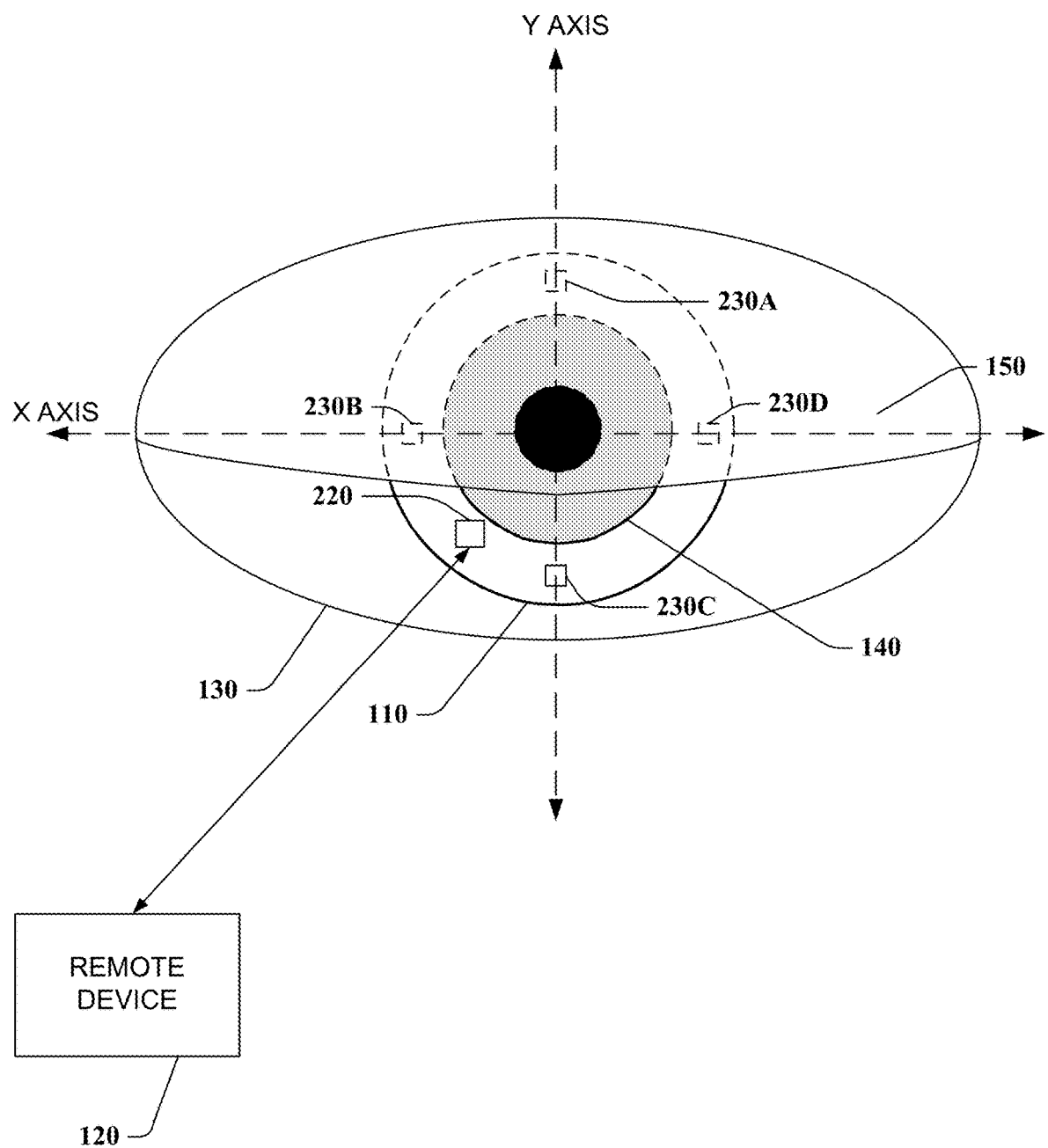
FIG. 3C illustrates a diagram of the close-up view of the portion of the exemplary non-limiting system of FIG. 3B with the eyelid partially closed an amount more than depicted in FIG. 3B in accordance with an implementation of this disclosure.

FIG. 3C corresponds to FIGS. 3A-B with eyelid 150 partially closed an amount more than depicted in FIG. 3B. As such, blink detection component 260 obtains state information corresponding to sensors 230A-B and 230D being covered by eyelid 150 and sensor 230C not being covered by eyelid 150. As depicted in FIGS. 3B-3C, state information can allow blink detection component 260 to determine (or infer) amount of partial blink that has occurred based on known or inferred positioning, for example using a coordinate system based upon the X and Y axis, of sensors 230A-D relative to each other or to a fixed position, such the geometric center of the multi-sensor contact lens 110.

Figure 3D:
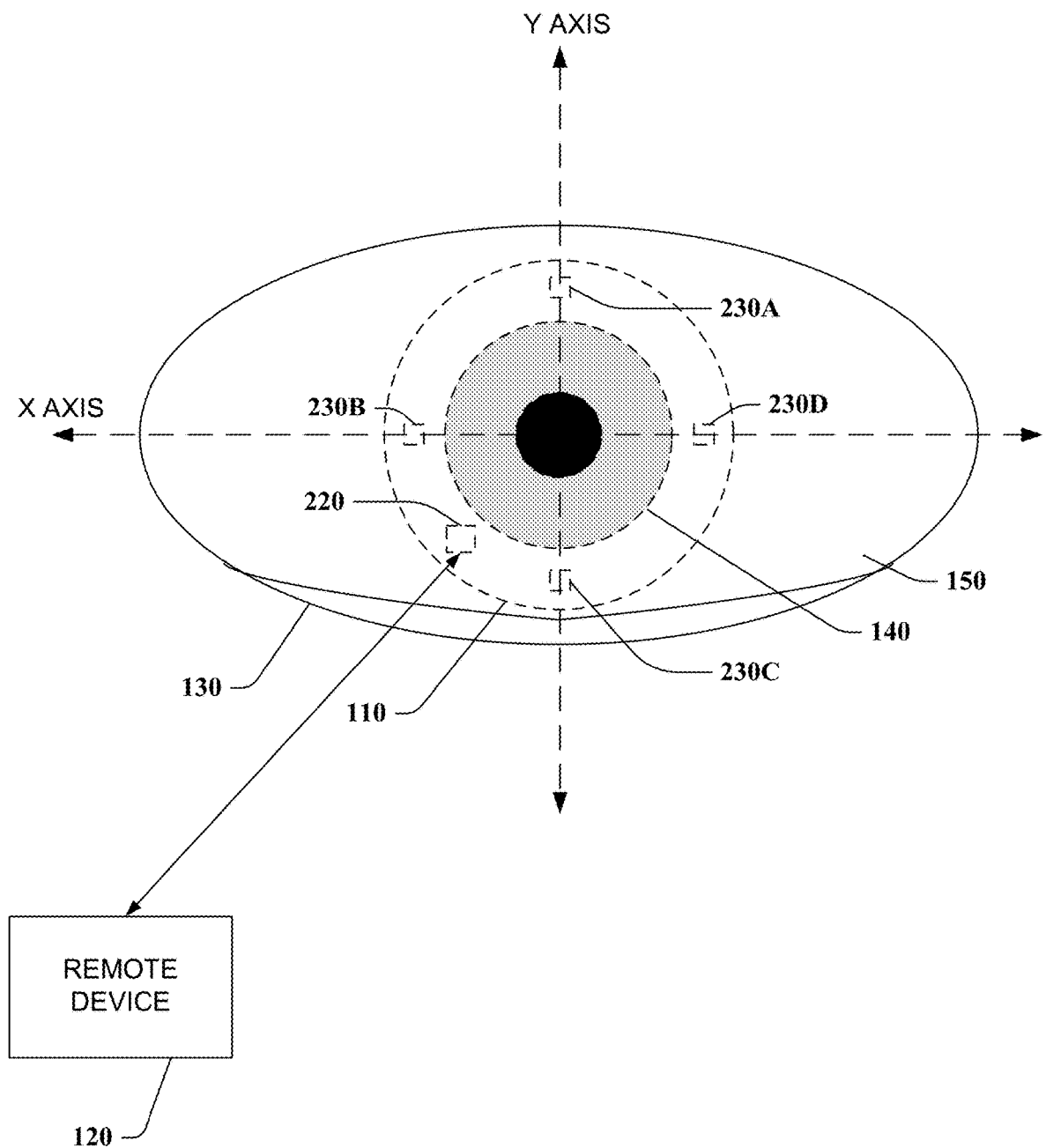
FIG. 3D illustrates a diagram of the close-up view of the portion of the exemplary non-limiting system of FIG. 3C with the eyelid closed in accordance with an implementation of this disclosure.

FIG. 3D corresponds to FIGS. 3A-C with eyelid 150 closed. As such, blink detection component 260 obtains state information corresponding to sensors 230A-D being covered by eyelid 150.

Figure 4A:
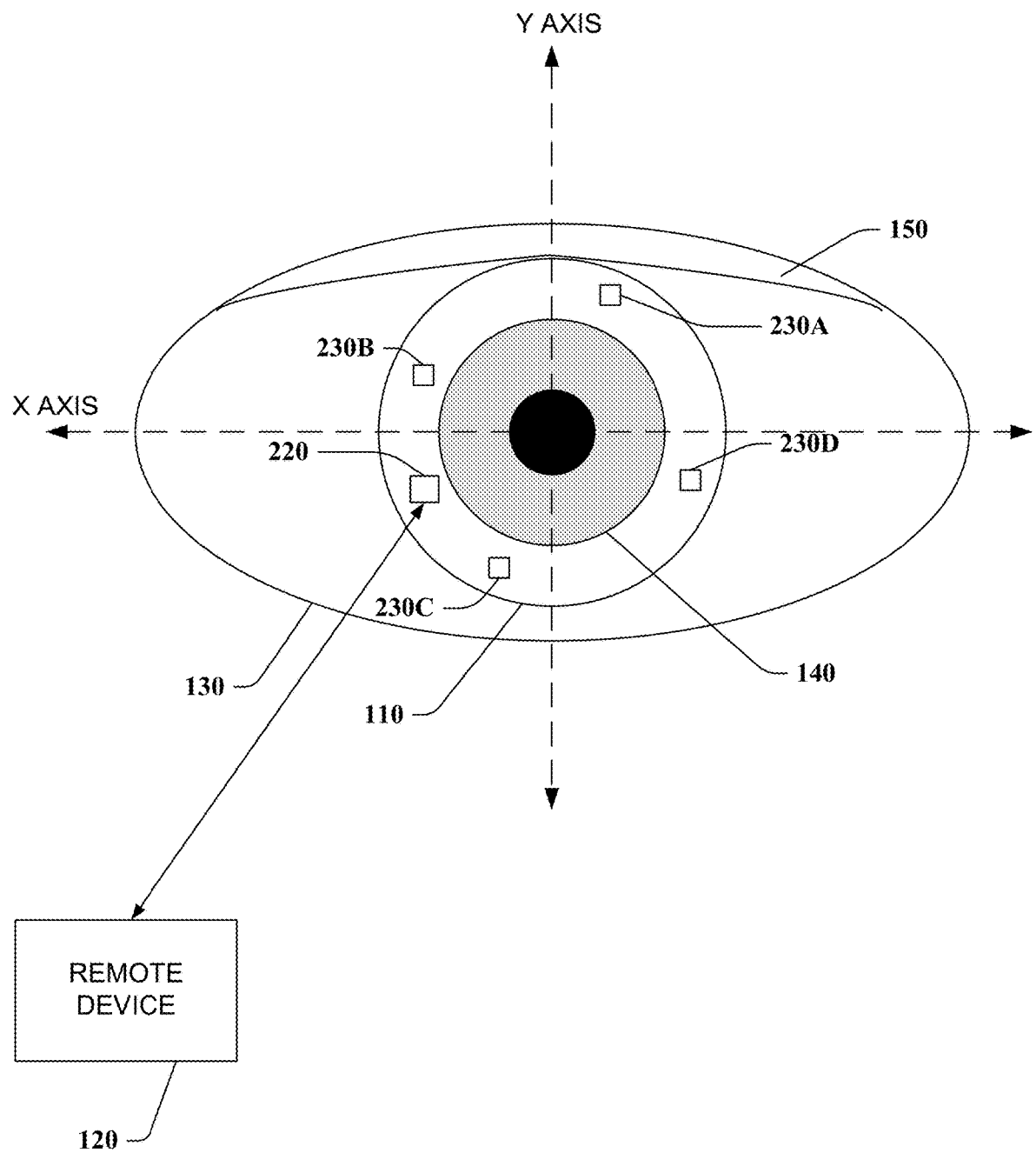
FIG. 4A illustrates a diagram of a close-up view of the portion of the exemplary non-limiting system of FIG. 3A being worn by a human user with multi-sensor contact lens in a different orientation in accordance with an implementation of this disclosure.

FIG. 4A corresponds to FIG. 3A with the multi-sensor contact lens 110 oriented at an angle of rotation a number of degrees about its geometric center. Eyelid 150 is open, and as such, blink detection component 260 obtains state information corresponding to sensors 230A-D not being covered by eyelid 150.

Figure 4B:
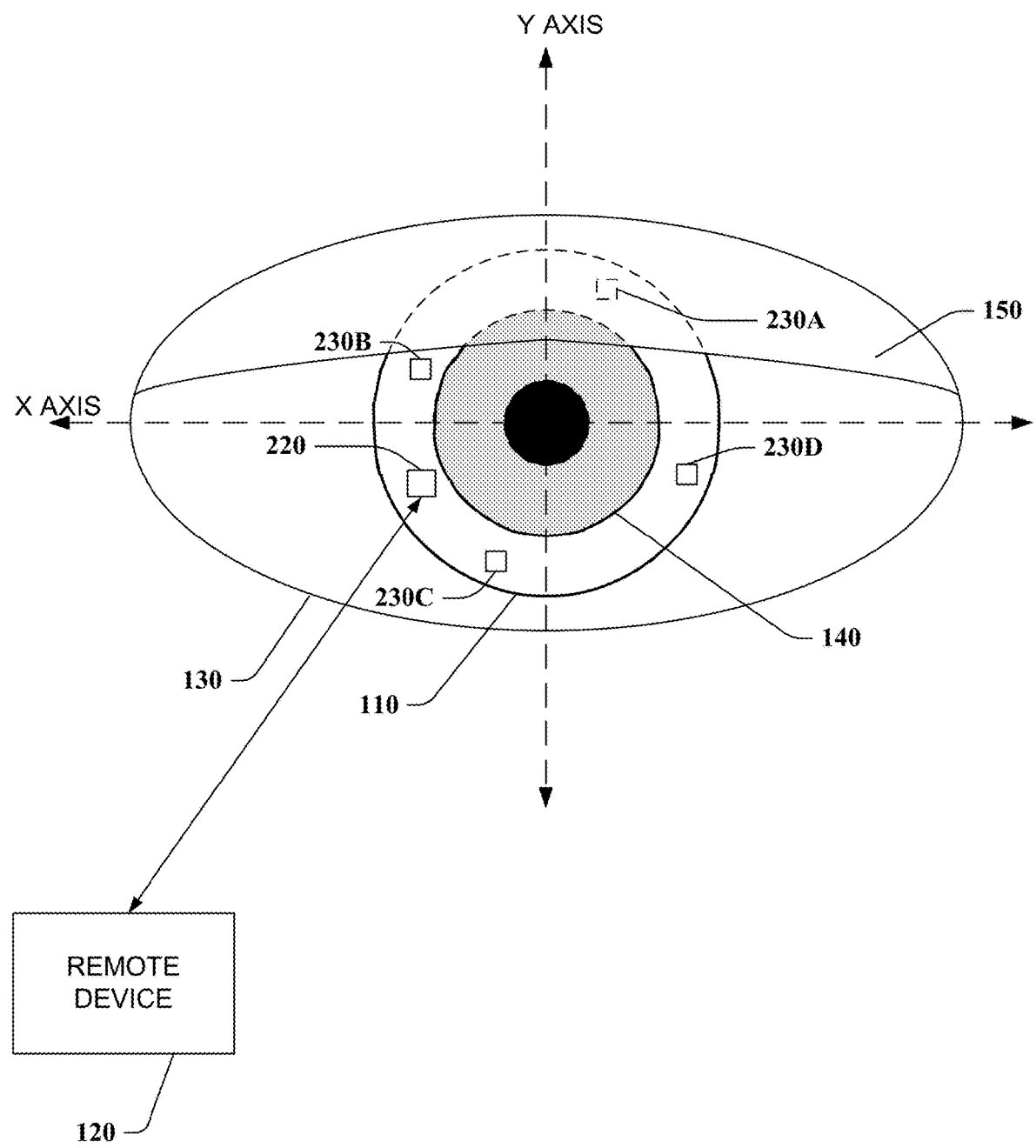
FIG. 4B illustrates a diagram of the close-up view of the portion of the exemplary non-limiting system of FIG. 4A with the eyelid partially closed in accordance with an implementation of this disclosure.

FIG. 4B corresponds to FIG. 4A with eyelid 150 partially closed. As such, blink detection component 260 obtains state information corresponding to sensor 230A covered by eyelid 150 and sensors 230B-D not covered by eyelid 150.

Figure 4C:
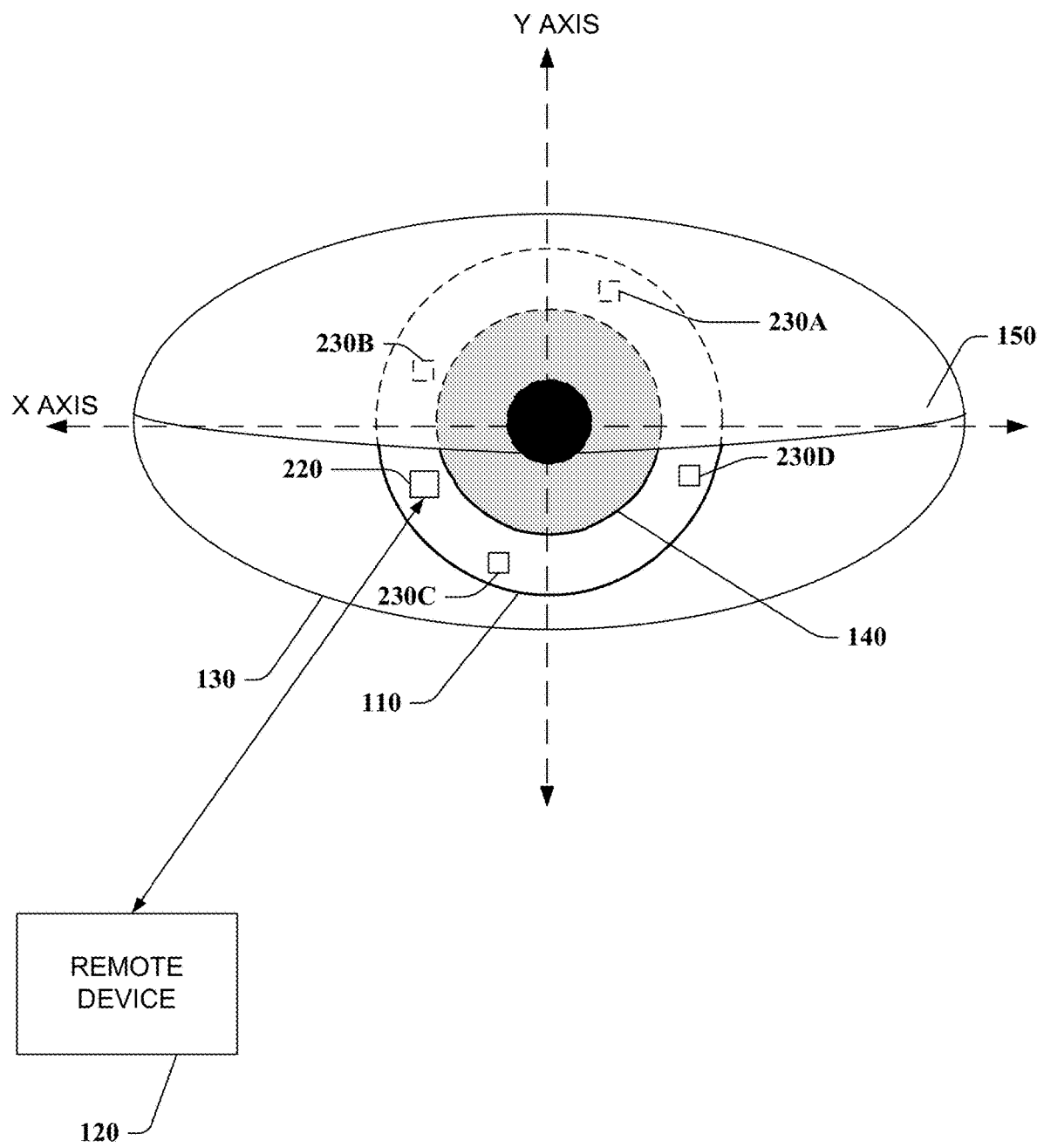
FIG. 4C illustrates a diagram of the close-up view of the portion of the exemplary non-limiting system of FIG. 4B with the eyelid partially closed an amount more than depicted in FIG. 4B in accordance with an implementation of this disclosure.

FIG. 4C corresponds to FIGS. 4A-B with eyelid 150 partially closed an amount more than depicted in FIG. 4B. As such, blink detection component 260 obtains state information corresponding to sensors 230A-B being covered by eyelid 150 and sensors 230C-D not being covered by eyelid 150.

Figure 4D:
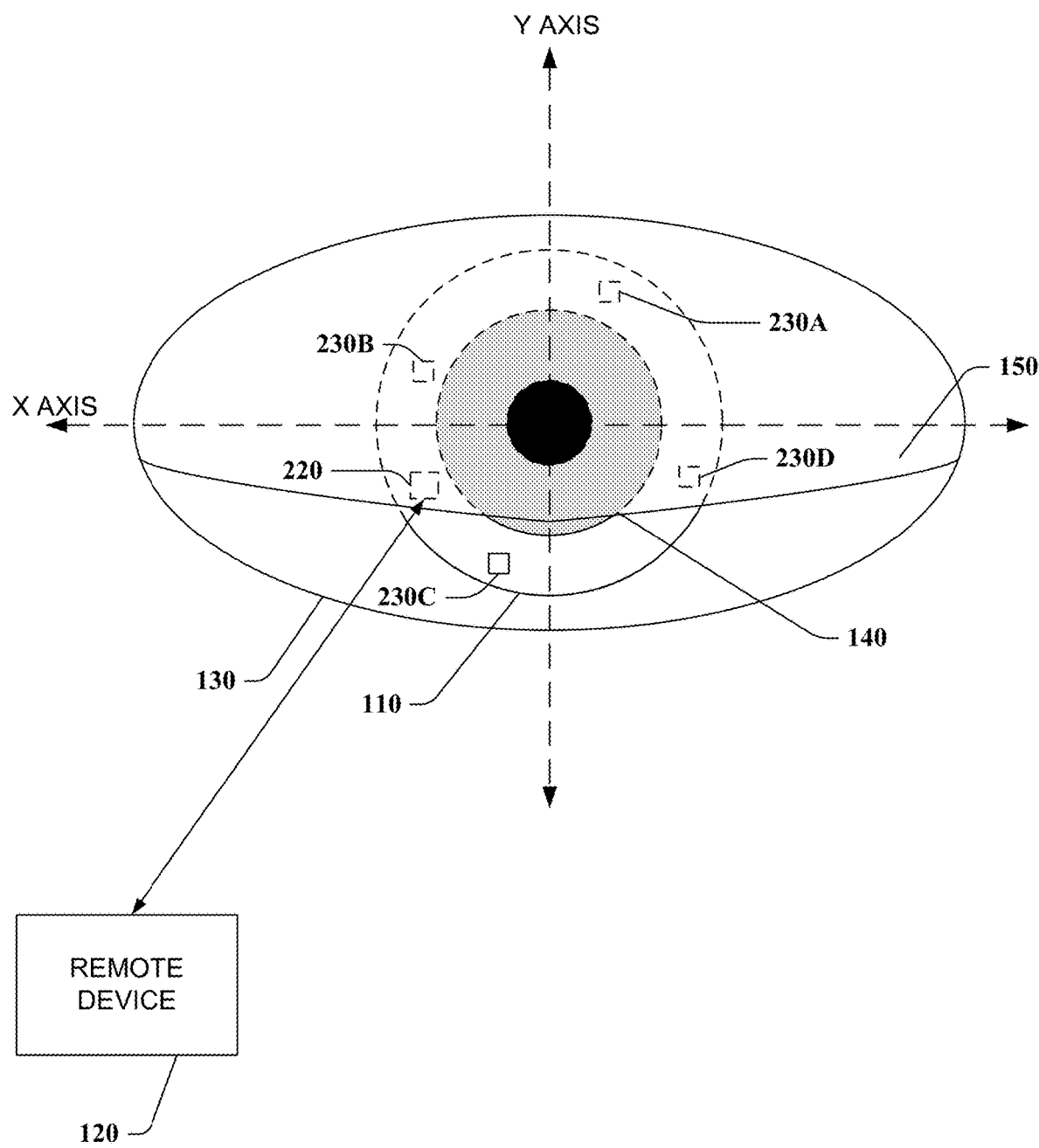
FIG. 4D illustrates a diagram of the close-up view of the portion of the exemplary non-limiting system of FIG. 4C with the eyelid partially closed an amount more than depicted in FIG. 4C in accordance with an implementation of this disclosure.

FIG. 4D corresponds to FIGS. 4A-C with eyelid 150 partially closed an amount more than depicted in FIG. 4C. As such, blink detection component 260 obtains state information corresponding to sensors 230A-B and 230D being covered by eyelid 150 and sensor 230C not being covered by eyelid 150. As depicted in FIGS. 4B-D versus 3B-C, the rotated orientation of multi-sensor contact lens allows for a finer precision or granularity with respect to determining (or inferring) the amount of partial blink that has occurred based on known or inferred positioning of sensors 230A-D.

Figure 4E:
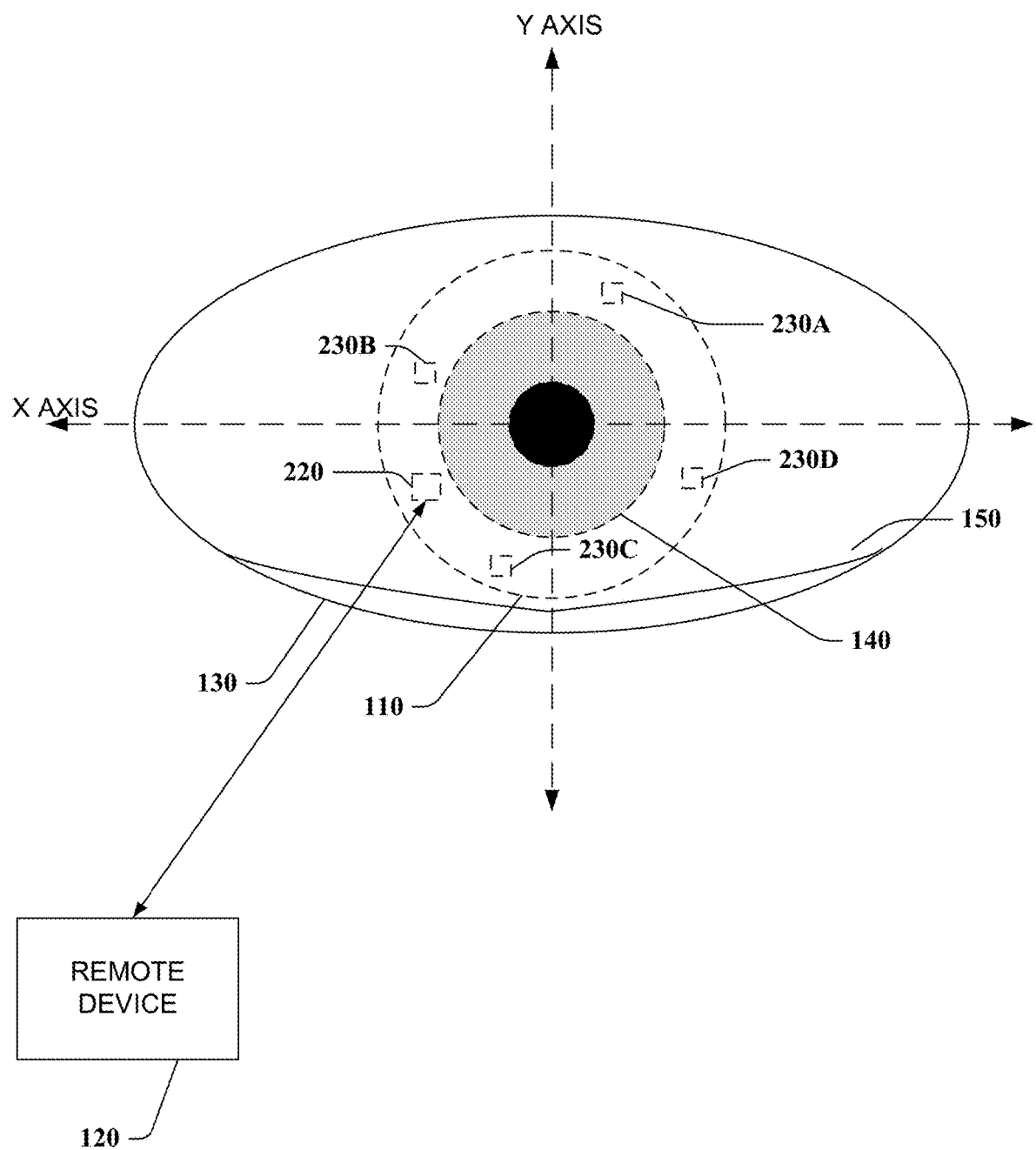
FIG. 4E illustrates a diagram of the close-up view of the portion of the exemplary non-limiting system of FIG. 4E with the eyelid closed in accordance with an implementation of this disclosure.

FIG. 4E corresponds to FIGS. 4A-D with eyelid 150 closed. As such, blink detection component 260 obtains state information corresponding to sensors 230A-D being covered by eyelid 150.

FIGS. 3A-D and 4A-E are non-limiting examples of configurations for sensors on multi-sensor contact lens 110. It is to be appreciated that any suitable number sensors 230 can be placed in any suitable location(s) of multi-sensor contact lens 110. It is to be further appreciated that, respective multi-sensor contact lens 110 in two eyes can have differing configurations of sensors 230.

Blink detection component 260 employs the state information to determine (or infer) a blink of eye 130. It is to be appreciated that blink detection component 260 can employ various algorithms and mathematical functions to determine eye blink information. In an embodiment, blink detection component 260 or sensor 230 can determine state information by employing data from sensor 230 in conjunction with a threshold to determined (or inferred) whether eyelid 150 is covering sensor 230. It is to be appreciated that a threshold can be any condition, for example, a greater than condition, less than condition, equal to condition, one or more ranges, or function. For example, if data from sensor 230 is below or equal to an eyelid covering threshold, it can be determined (or inferred) that eyelid 150 is covering sensor 230. In another example, if data from sensor 230 is within a range indicated by the eyelid covering threshold, it can be determined (or inferred) that eyelid 150 is covering sensor 230. In addition, blink detection component 260 can employ state information obtained at multiple points in time to determine duration of eyelid 150 covering sensor 230. Blink detection component 260 can employ duration of eyelid closure over a period of time, for example at consecutive points in time indicating eyelid closure, to determine whether a blink has occurred or whether the eyelid is closed, for example, during a nap. Blink detection component 260 can employ an eyelid closure duration threshold to indicate whether a blink has occurred.

For example, if a period of time of eyelid closure is below an eyelid closure duration threshold, it can be determined (or inferred) that a blink has occurred. In another example, if a period of time of eyelid closure is within a range indicated by eyelid closure duration threshold, it can be determined (or inferred) that a blink has occurred. In addition, blink detection component 260 can track the respective times that respective sensors 230 indicate a state change indicating covering or uncovering by eyelid 150 during a single eye blink along with known positions of the respective sensors 230 to determine a speed at which the eye blink occurred. Blink detection component 260 can employ speed at which an eye blink occurred, for example, to determine (or infer) an involuntary eye blink versus a voluntary eye blink, such as when a user is selectively blinking. Additionally, blink detection component 260 can employ an order in which sensors 230 are covered or uncovered to determine (or infer) an eye blink. For example, if a sensor 230 indicates a state change that is not in alignment with an expected order or state changes for sensors 230 during an eye blink, blink detection component can determine (or infer) that an eye blink did not occur, such during a faulty sensor reading or a sensor 230 being covered by something other than an eyelid.

Furthermore, blink detection component 260 can track eye blinks over a period of time to identify patterns of eye blinking for one or both eyes. It is to be appreciated that pattern of eye blinking can include number of blinks in one or both eyes, duration of blinks in one or both eyes, pause between blinks in one or both eyes, partial blinks (an amount of partial blink) in one or both eyes, order of blinks in one or both eyes, or speed of eye blink. In an example, blink detection component 260 can identify a known pattern of blinking for one or both eyes that correlates to an associated command input, from a library of commands, of the multi-sensor contact lens 110 or remote device 120. For example, a library of commands can include one or more commands with a respective pattern of eye blinking that corresponds to a respective command.

Referring back to FIG. 2H, interface component 270 can communicate eye blink information, such as a determined (or inferred) blink of an eye, speed of an eye blink, an identified pattern of eye blinking, command input associated with an identified pattern of eye blinking, or respective times or order that respective sensors 230 indicate a state change indicating covering or uncovering by eyelid 150, to remote device 120 using one or more transceivers 280. Furthermore, interface component 270 can receive data or commands from remote device 120 using the one or more transceivers 280. For example, interface component 270 can receive a request for eye blink information from remote device 120 and respond to the request with eye blink information.

Orientation component 265 can employ eye blink information to determine (or infer) orientation of a multi-sensor contact lens 110 when worn in an eye. It is to be appreciated that orientation component 265 can employ various algorithms and mathematical functions to determine orientation information. For example, the order that respective sensors 230 indicate a state change indicating covering or uncovering by eyelid 150 can allow for determining (or inferring) rotational orientation of multi-sensor contact lens 110 about its geometric center. Referring to FIGS. 3A-D, sensor 230A is covered first as eyelid 150 closes during a blink, then next sensors 230B and 230D are covered substantially simultaneously, and then sensor 230C is covered, and visa-versa as eyelid 150 opens. Given known locations of sensors 230A-D relative to each other or a geometric center of multi-sensor contact lens 110, this ordering can provide an indication that sensor 230A is oriented above sensors 230B-D, and that sensors 230B and 230D are aligned parallel to the X axis below sensor 230A and above sensor 230C. Orientation component 265 can employ this information to determine (or infer) that multi-sensor contact lens 110 is oriented as depicted in FIGS. 3A-D. Referring to FIGS. 4A-E, sensor 230A is covered first as eyelid 150 blinks, then sensor 230B is covered, followed by sensor 230D, and then sensor 230C is covered, and visa-versa as eyelid 150 opens. Given the known locations of sensors 230A-D relative to each other or the geometric center of multi-sensor contact lens 110, this ordering can provide an indication that sensor 230A is oriented above sensors 230B, which is oriented above sensor 230D, which is oriented above sensor 230C. Orientation component 265 can employ this information to determine (or infer) that multi-sensor contact lens 110 is oriented as depicted in FIGS. 4A-E, within a window of error. The window of error can be, for example, a rotational angle window surrounding a sensor 230 within which multi-sensor contact lens 110 can rotate about its geometric center while sensor 230 remains above or below a neighboring sensor 230. It is to be appreciated that this window of error can be reduced as density of sensors increases on or within multi-sensor contact lens 110, for example, distributed around the periphery of the multi-sensor contact lens 110 or linearly across one or more portions of the multi-sensor contact lens 110. It is further to be appreciated that a partial blink covering at least two sensors 230 can be sufficient to determine (or infer) orientation of multi-sensor contact lens 110 within a window of error.

In addition, orientation component 265 can employ a predetermined blink speed indicative of the speed at which eyelid 150 moves along the Y axis during an eye blink to increase precision of estimation of position of two sensors 230 relative to each other and the geometric center of multi-sensor contact lens 110. For example the predetermined blink speed can be an average speed of a human user or non-human user eye blink. In another example, the predetermined blink speed can be determined as part of a calibration operation of multi-sensor contact lens 110 when worn in an eye 130. It is to be appreciated that predetermined blink speed can be based upon any suitable mechanism for setting, determining, or inferring speed of an eye blink.

Figure 5:
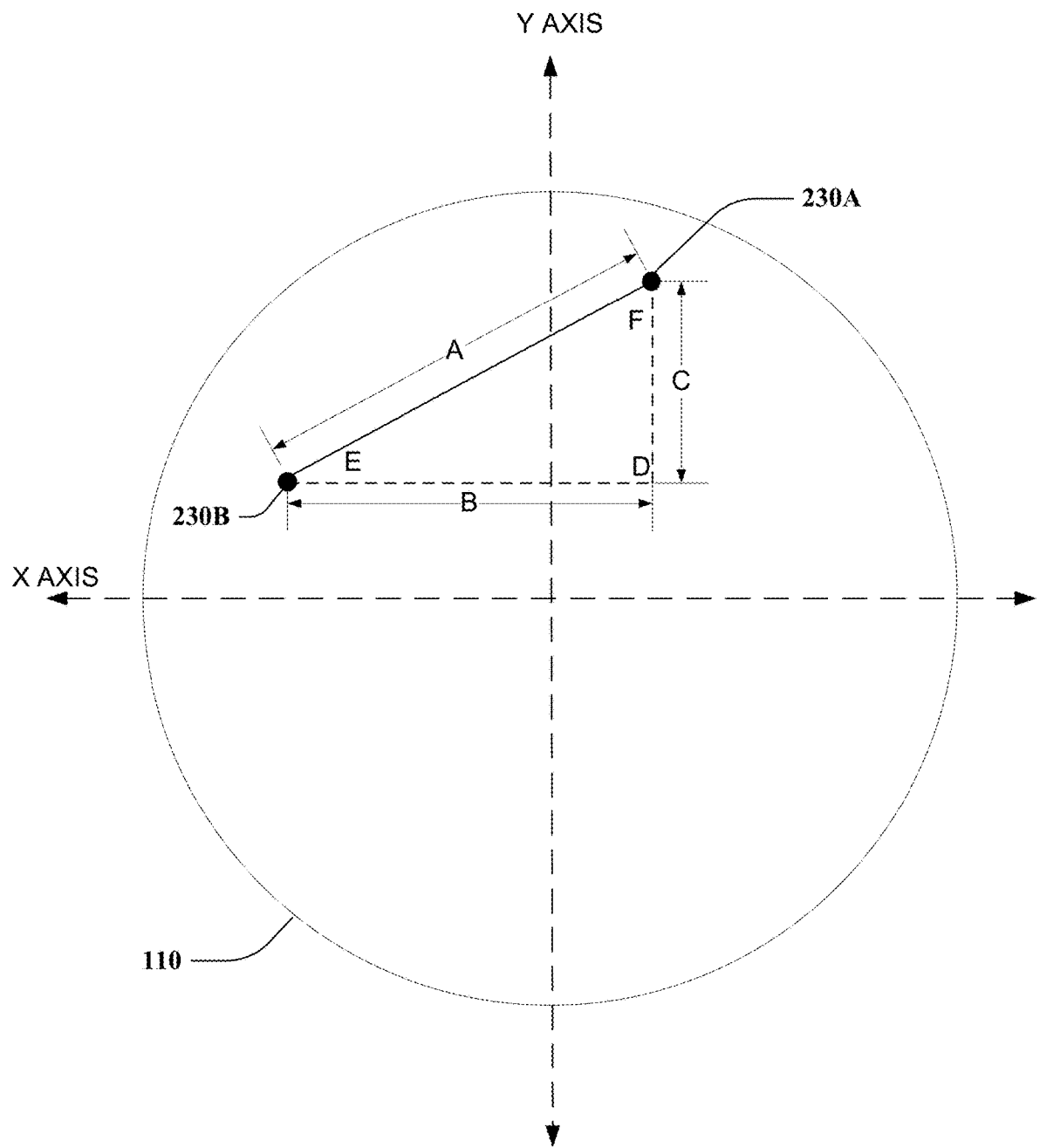
FIG. 5 illustrates a diagram of a multi-sensor contact lens with two sensors showing variables for determining orientation when using a predetermined blink speed in accordance with an implementation of this disclosure.

Referring to FIG. 5 is depicted multi-sensor contact lens 110 with two sensors 230A-B worn in eye 130. Given known positions of sensors 230A-B relative to each other and a geometric center of multi-sensor contact lens 110, distance A can be determined (or inferred) by orientation component 265. Additionally, employing a predetermined blink speed and tracked times of sensors 230A-B indicating a common state change to covered or uncovered by an eyelid 150, distance C can be determined (or inferred) by orientation component 265. With angle D known to be a 90 degree angle, distance B and angles E and F can be determined (or inferred) by orientation component 265. Using the above determined information, orientation component 265 can determine (or infer) the positions of sensor 230A-B relative to the X and Y axis having an origin at the geometric center of multi-sensor contact lens 110. It is to be appreciated that orientation information can include determined (or inferred) positions of sensors 230 relative to a coordinate system, a rotational angle of multi-sensor contact lens 110 about its geometric center, or any other suitable indication for orientation of multi-sensor contact lens 110. Additionally, orientation information can be included in eye blink information. Interface component 270 can communicate orientation information to remote device 120.

Furthermore, multi-sensor contact lens 110 or remote device 120 can employ orientation information to send commands to or interpret data from one or more components (shown or not shown) of multi-sensor contact lens 110. For example, multi-sensor contact lens 110 can have one or more LEDs (not shown) visible to a user when worn that have specific meaning based upon their position in the user's view. Orientation information can be employed to control which LEDs to activate. In another example, multi-sensor contact lens 110 can have a display (not shown) visible to the user when worn. Orientation information can be employed to control presentation of content, for example, to maintain a properly oriented display. In a further example, user health diagnostic components (not shown), such as a camera directed to the interior of the eye, may require specific positioning or need to be interpreted differently based upon position. Orientation information can allow for determination of the reliability of diagnostic data or when to initiate a diagnostic test.

Power component 275 can include any suitable power source that can manage, receive, generate, store, and/or distribute necessary electrical power for the operation of various components of multi-sensor contact lens 110. For example, power component 275 can include but is not limited to a battery, a capacitor, a solar power source, radio frequency power source, electrochemical power source, temperature power source, or mechanically derived power source (e.g., MEMs system). In another example, power component 275 receives or generates power from one or more sensors 230. Transceiver 280 can transmit and receive information to and from, or within multi-sensor contact lens 110. In some embodiments, transceiver 280 can include an RF antenna.

It is to be appreciated that in accordance with one or more implementations described in this disclosure, users can opt-in or opt-out of providing personal information, demographic information, location information, proprietary information, sensitive information, or the like in connection with data gathering aspects. Moreover, one or more implementations described herein can provide for anonymizing collected, received, or transmitted data.

Figure 6:
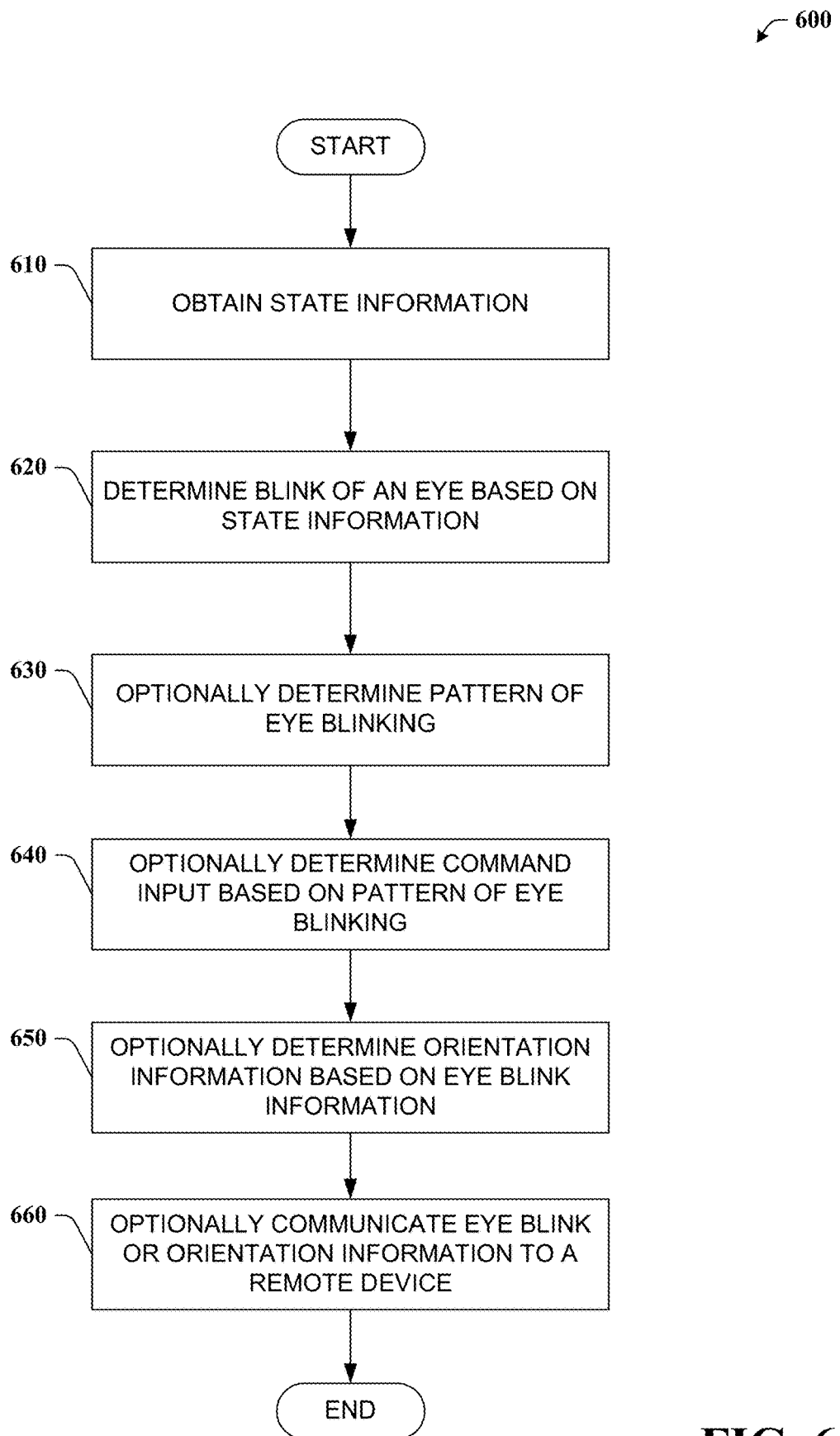
FIG. 6 illustrates an exemplary non-limiting flow diagram for detecting blinking of an eye or orientation of a contact lens in accordance with an implementation of this disclosure.

FIG. 6 illustrates various methodologies in accordance with certain disclosed aspects. While, for purposes of simplicity of explanation, the methodologies are shown and described as a series of acts, it is to be understood and appreciated that the disclosed aspects are not limited by the order of acts, as some acts may occur in different orders and/or concurrently with other acts from that shown and described herein. For example, those skilled in the art will understand and appreciate that a methodology can alternatively be represented as a series of interrelated states or events, such as in a state diagram. Moreover, not all illustrated acts may be required to implement a methodology in accordance with certain disclosed aspects. Additionally, it is to be further appreciated that the methodologies disclosed hereinafter and throughout this disclosure are capable of being stored on an article of manufacture to facilitate transporting and transferring such methodologies to computers.

Referring to FIG. 6, an exemplary method 600 for determining blinking of an eye or orientation of a contact lens is depicted. At reference numeral 610, state information related to sensors of a multi-sensor contact lens(es) worn in one or more eyes is obtained (e.g. by blink detection component 260, sensor 230, or control circuit 220). At reference numeral 620, one or more full or partial blinks of the one or more eyes is determined (or inferred) based on the state information (e.g. by a blink detection component 260 or control circuit 220). At reference numeral 630, an optional act of identifying a pattern of blinking of the one or more eyes is performed (e.g. by a blink detection component 260 or control circuit 220). At reference numeral 640, an optional act of determining a command input associated with the identified pattern of eye blinking is performed (e.g. by a blink detection component 260 or control circuit 220). At reference numeral 650, an optional act of determining (or inferring) orientation information for the multi-sensor contact lens(es) worn in one or more eyes based upon the determined (or inferred) full or partial blink or eye blink information derived therefrom is performed (e.g. by an orientation component 265 or control circuit 220). At reference numeral 660, an optional act of communicating eye blink or orientation information to a remote device is performed (e.g. by an interface component 270 or control circuit 220).

Exemplary Networked and Distributed Environments

One of ordinary skill in the art can appreciate that the various embodiments described herein can be implemented in connection with any computer or other client or server device, which can be deployed as part of a computer network or in a distributed computing environment, and can be connected to any kind of data store where media may be found. In this regard, the various embodiments described herein can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computing devices and systems. These resources and services include the exchange of information, cache storage and disk storage for objects, such as files. These resources and services can also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the various embodiments of this disclosure.

Figure 7:
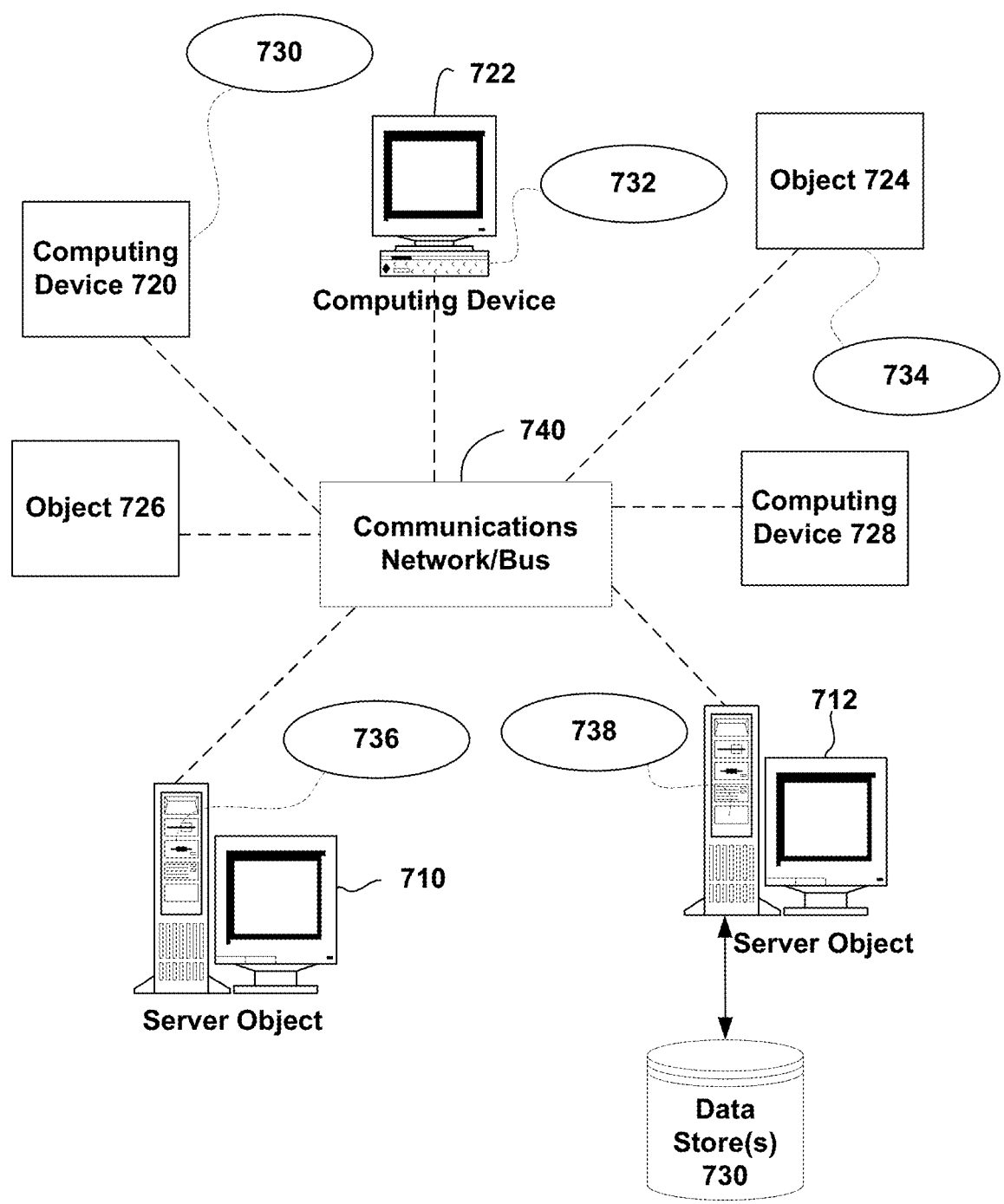
FIG. 7 is a block diagram representing an exemplary non-limiting networked environment in which the various embodiments can be implemented.

FIG. 7 provides a schematic diagram of an exemplary networked or distributed computing environment. The distributed computing environment comprises computing objects 710, 712, etc. and computing objects or devices 720, 722, 724, 726, 728, etc., which may include programs, methods, data stores, programmable logic, etc., as represented by applications 730, 732, 734, 736, 738. It can be appreciated that computing objects 710, 712, etc. and computing objects or devices 720, 722, 724, 726, 728, etc. may comprise different devices, such as personal digital assistants (PDAs), audio/video devices, mobile phones, MP3 players, personal computers, laptops, tablets, etc.

Each computing object 710, 712, etc. and computing objects or devices 720, 722, 724, 726, 728, etc. can communicate with one or more other computing objects 710, 712, etc. and computing objects or devices 720, 722, 724, 726, 728, etc. by way of the communications network 740, either directly or indirectly. Even though illustrated as a single element in FIG. 7, network 740 may comprise other computing objects and computing devices that provide services to the system of FIG. 7, and/or may represent multiple interconnected networks, which are not shown. Each computing object 710, 712, etc. or computing objects or devices 720, 722, 724, 726, 728, etc. can also contain an application, such as applications 730, 732, 734, 736, 738, that might make use of an API, or other object, software, firmware and/or hardware, suitable for communication with or implementation of various embodiments of this disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any suitable network infrastructure can be used for exemplary communications made incident to the systems as described in various embodiments herein.

Thus, a host of network topologies and network infrastructures, such as client/server, peer-to-peer, or hybrid architectures, can be utilized. The "client" is a member of a class or group that uses the services of another class or group. A client can be a computer process, e.g., roughly a set of instructions or tasks, that requests a service provided by another program or process. A client process may utilize the requested service without having to "know" all working details about the other program or the service itself.

In a client/server architecture, particularly a networked system, a client can be a computer that accesses shared network resources provided by another computer, e.g., a server. In the illustration of FIG. 7, as a non-limiting example, computing objects or devices 720, 722, 724, 726, 728, etc. can be thought of as clients and computing objects 710, 712, etc. can be thought of as servers where computing objects 710, 712, etc. provide data services, such as receiving data from client computing objects or devices 720, 722, 724, 726, 728, etc., storing of data, processing of data, transmitting data to client computing objects or devices 720, 722, 724, 726, 728, etc., although any computer can be considered a client, a server, or both, depending on the circumstances. Any of these computing devices may be processing data, or requesting transaction services or tasks that may implicate the techniques for systems as described herein for one or more embodiments.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server. Any software objects utilized pursuant to the techniques described herein can be provided standalone, or distributed across multiple computing devices or objects.

In a network environment in which the communications network/bus 740 is the Internet, for example, the computing objects 710, 712, etc. can be Web servers, file servers, media servers, etc. with which the client computing objects or devices 720, 722, 724, 726, 728, etc. communicate via any of a number of known protocols, such as the hypertext transfer protocol (HTTP). Objects 710, 712, etc. may also serve as client computing objects or devices 720, 722, 724, 726, 728, etc., as may be characteristic of a distributed computing environment.

Exemplary Computing Device

As mentioned, advantageously, the techniques described herein can be applied to any suitable device. It is to be understood, therefore, that handheld, portable and other computing devices and computing objects of all kinds are contemplated for use in connection with the various embodiments. Accordingly, the computer described below in FIG. 8 is but one example of a computing device that can be employed with implementing one or more of the systems or methods shown and described in connection with FIGS. 1-8. Additionally, a suitable server can include one or more aspects of the below computer, such as a media server or other media management server components.

Although not required, embodiments can partly be implemented via an operating system, for use by a developer of services for a device or object, and/or included within application software that operates to perform one or more functional aspects of the various embodiments described herein. Software may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is to be considered limiting.

FIG. 8 thus illustrates an example of a suitable computing system environment 800 in which one or aspects of the embodiments described herein can be implemented, although as made clear above, the computing system environment 800 is only one example of a suitable computing environment and is not intended to suggest any limitation as to scope of use or functionality. Neither is the computing environment 800 be interpreted as having any dependency or requirement relating to any one or combination of components illustrated in the exemplary operating environment 800.

With reference to FIG. 8, an exemplary computing device for implementing one or more embodiments in the form of a computer 810 is depicted. Components of computer 810 may include, but are not limited to, a processing unit 820, a system memory 830, and a system bus 822 that couples various system components including the system memory to the processing unit 820.

Computer 810 typically includes a variety of computer readable media and can be any available media that can be accessed by computer 810. The system memory 830 may include computer storage media in the form of volatile and/or nonvolatile memory such as read only memory (ROM) and/or random access memory (RAM). By way of example, and not limitation, system memory 830 may also include an operating system, application programs, other program modules, and program data.

A user can enter commands and information into the computer 810 through input devices 840, non-limiting examples of which can include a keyboard, keypad, a pointing device, a mouse, stylus, touchpad, touchscreen, trackball, motion detector, camera, microphone, joystick, game pad, scanner, or any other device that allows the user to interact with computer 810. A monitor or other type of display device is also connected to the system bus 822 via an interface, such as output interface 850. In addition to a monitor, computers can also include other peripheral output devices such as speakers and a printer, which may be connected through output interface 850.

The computer 810 may operate in a networked or distributed environment using logical connections to one or more other remote computers, such as remote computer 860. The remote computer 860 may be a personal computer, a server, a router, a network PC, a peer device or other common network node, or any other remote media consumption or transmission device, and may include any or all of the elements described above relative to the computer 810. The logical connections depicted in FIG. 8 include a network 862, such local area network (LAN) or a wide area network (WAN), but may also include other networks/buses e.g., cellular networks.

As mentioned above, while exemplary embodiments have been described in connection with various computing devices and network architectures, the underlying concepts may be applied to any network system and any computing device or system in which it is desirable to publish or consume media in a flexible way.

Also, there are multiple ways to implement the same or similar functionality, e.g., an appropriate API, tool kit, driver code, operating system, control, standalone or downloadable software object, etc. which enables applications and services to take advantage of the techniques described herein. Thus, embodiments herein are contemplated from the standpoint of an API (or other software object), as well as from a software or hardware object that implements one or more aspects described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the aspects disclosed herein are not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used in either the detailed description or the claims, for the avoidance of doubt, such terms are intended to be inclusive in a manner similar to the term "comprising" as an open transition word without precluding any additional or other elements.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

As mentioned, the various techniques described herein may be implemented in connection with hardware or software or, where appropriate, with a combination of both. As used herein, the terms "component," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function (e.g., coding and/or decoding); software stored on a computer readable medium; or a combination thereof.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it is to be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In order to provide for or aid in the numerous inferences described herein (e.g. inferring relationships between metadata or inferring topics of interest to users), components described herein can examine the entirety or a subset of the data to which it is granted access and can provide for reasoning about or infer states of the system, environment, etc. from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data.

Such inference can result in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines, etc.) can be employed in connection with performing automatic and/or inferred action in connection with the claimed subject matter.

A classifier can map an input attribute vector, x=(x1, x2, x3, x4, xn), to a confidence that the input belongs to a class, as by f(x)=confidence(class). Such classification can employ a probabilistic and/or statistical-based analysis (e.g., factoring into the analysis utilities and costs) to prognose or infer an action that a user desires to be automatically performed. A support vector machine (SVM) is an example of a classifier that can be employed. The SVM operates by finding a hyper-surface in the space of possible inputs, where the hyper-surface attempts to split the triggering criteria from the non-triggering events. Intuitively, this makes the classification correct for testing data that is near, but not identical to training data. Other directed and undirected model classification approaches include, e.g., naïve Bayes, Bayesian networks, decision trees, neural networks, fuzzy logic models, and probabilistic classification models providing different patterns of independence can be employed. Classification as used herein also is inclusive of statistical regression that is utilized to develop models of priority.

In view of the exemplary systems described above, methodologies that may be implemented in accordance with the described subject matter will be better appreciated with reference to the flowcharts of the various figures. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, not all illustrated blocks may be required to implement the methodologies described hereinafter.

In addition to the various embodiments described herein, it is to be understood that other similar embodiments can be used or modifications and additions can be made to the described embodiment(s) for performing the same or equivalent function of the corresponding embodiment(s) without deviating there from. Still further, multiple processing chips or multiple devices can share the performance of one or more functions described herein, and similarly, storage can be effected across a plurality of devices. Accordingly, the invention is not to be limited to any single embodiment, but rather can be construed in breadth, spirit and scope in accordance with the appended claims.

The invention claimed is:

1. A contact lens device, comprising:
a substrate;
a plurality of sensors disposed on or within the substrate; and
a control circuit disposed within the contact lens device and coupled to the plurality of sensors, the control circuit including instructions stored thereon that, in response to execution, cause the contact lens device to perform operations including:
determining when a first sensor in the plurality of sensors measures a first eyelid covering threshold, in response to a first position of an eyelid;
determining when a second sensor in the plurality of sensors measures a second eyelid covering threshold, in response to a second position of the eyelid;
determining that the eyelid is partially closed, when the first sensor measures the first eyelid covering threshold and the second sensor does not measure the second eyelid covering threshold; and
issuing a command to an electronic component disposed in the contact lens in response to determining that the eyelid is partially closed.

2. The contact lens device of claim 1, wherein the electronic component includes an interface component configured to communicate information to a remote device.

3. The contact lens device of claim 2, wherein the interface component includes a transceiver.

4. The contact lens device of claim 1, wherein the electronic component includes a power component coupled to generate power for the plurality of sensors.

5. The contact lens device of claim 4, wherein the power component includes at least one of a battery, a capacitor, or a solar powered device.

6. The contact lens device of claim 1, further comprising an orientation component configured to determine orientation information of the contact lens device based upon a covering or an uncovering order of one or more of the plurality of sensors by the eyelid, wherein the orientation component includes at least one of hardware logic or software instructions.

7. The contact lens device of claim 1, wherein the first eyelid covering threshold occurs when the eyelid covers at least part of the first sensor.

8. The contact lens device of claim 1, wherein the plurality of sensors include at least one of:
a photodiode coupled to the control circuit to measure an amount of light received by the photodiode;
a pressure sensor coupled to the control circuit to measure a pressure change proximate to the pressure sensor;
a conductivity sensor coupled to the control circuit to measure a change in conductivity of a tear film;
a temperature sensor coupled to the control circuit to measure a change in temperature; or
an electric field sensor coupled to the control circuit to measure a change in capacitance.

9. The contact lens device of claim 1, wherein the control circuit further includes instructions stored thereon that, in response to execution, cause the contact lens device to perform operations including:
determining that the eyelid is closed when the first sensor measures the first eyelid covering threshold and the second sensor measures the second eyelid covering threshold.

10. A method of operating a contact lens device, comprising:
determining, using a control circuit, when a first sensor in a plurality of sensors measures a first eyelid covering threshold in response to a first position of an eyelid, wherein the plurality of sensors and the control circuit are disposed within the contact lens;
determining, using the control circuit, when a second sensor in the plurality of sensors measures a second eyelid covering threshold in response to a second position of the eyelid;
determining that the eyelid is partially closed, when the first sensor measures the first eyelid covering threshold and the second sensor does not measure the second eyelid covering threshold; and
issuing a command to an electronic component disposed in the contact lens in response to determining that the eyelid is partially closed.

11. The method of claim 10, further comprising communicating information to a remote device using an interface component, wherein the interface component includes the electronic component.

12. The method of claim 10, further comprising generating power for the plurality of sensors with a power component coupled to the plurality of sensors, wherein the power component includes the electronic component.

13. The method of claim 12, wherein generating the power includes using at least one of a battery, a capacitor, or a solar powered device disposed within the power component.

14. The method of claim 10, further comprising determining orientation information about the contact lens device using an orientation component, wherein the orientation component includes the electronic component.

15. The method of claim 10, wherein determining when the first sensor measures the first eyelid covering threshold includes at least one of:
measuring an amount of light received by a photodiode coupled to the control circuit;
measuring a pressure change received by a pressure sensor coupled to the control circuit;
measuring a change in conductivity of a tear film using a conductivity sensor coupled to the control circuit;
measuring a change in temperature using a temperature sensor coupled to the control circuit; or
measuring a change in capacitance using an electric field sensor coupled to the control circuit.

16. The method of claim 10, further comprising determining that the eyelid is closed when the first sensor measures the first eyelid covering threshold and the second sensor measures the second eyelid covering threshold.

17. The method of claim 10, wherein the first eyelid covering threshold occurs when the eyelid covers at least part of the first sensor.

* * * * *